(12) United States Patent
Manandhar et al.

(10) Patent No.: US 11,612,682 B2
(45) Date of Patent: *Mar. 28, 2023

(54) ERGONOMIC TUBING ATTACHMENT FOR MEDICAL APPARATUS

(71) Applicant: Integra LifeSciences Enterprises, LLLP, Princeton, NJ (US)

(72) Inventors: Prakash Manandhar, Lawrence, MA (US); Daniel J. Cotter, North Easton, MA (US); Robert A. Ketelhohn, Dunstable, MA (US); Peter L. Gould, Nashua, NH (US); Todd Metivier, Nashua, NH (US)

(73) Assignee: Integra LifeSciences Enterprises, LLLP, Princeton, NJ (US)

( * ) Notice: Subject to any disclaimer, the term of this patent is extended or adjusted under 35 U.S.C. 154(b) by 744 days.

This patent is subject to a terminal disclaimer.

(21) Appl. No.: 16/550,788

(22) Filed: Aug. 26, 2019

(65) Prior Publication Data

US 2019/0374690 A1    Dec. 12, 2019

Related U.S. Application Data

(63) Continuation of application No. 15/600,115, filed on May 19, 2017, now Pat. No. 10,391,210, which is a
(Continued)

(51) Int. Cl.
*A61M 1/00* (2006.01)
*A61B 1/00* (2006.01)
(Continued)

(52) U.S. Cl.
CPC ............ *A61M 1/86* (2021.05); *A61B 1/0051* (2013.01); *A61B 1/00131* (2013.01);
(Continued)

(58) Field of Classification Search
CPC ..... A61M 1/86; A61M 1/774; A61B 1/00131; A61B 1/00135; A61B 1/0051;
(Continued)

(56) References Cited

U.S. PATENT DOCUMENTS

| 4,063,557 A | 12/1977 | Wuchinich et al. |
| 4,223,676 A | 9/1980 | Wuchinich et al. |

(Continued)

FOREIGN PATENT DOCUMENTS

| CN | 103826568 A | 5/2014 |
| EP | 1607075 | 12/2005 |

(Continued)

OTHER PUBLICATIONS

International Search Report and Written Opinion for PCT/IB2017/052382 dated Aug. 17, 2 017.
(Continued)

*Primary Examiner* — Howard D Brown, Jr.
(74) *Attorney, Agent, or Firm* — Gray Ice Higdon

(57) ABSTRACT

An ergonomic attachment system for connecting an irrigation tube or an aspiration tube to a surgical handpiece that reduces surgeon wrist fatigue due to tubing twist. The tube is connected to the handpiece through a swivel joint which allows the tube to rotate circumferentially with respect to the handpiece and self-adjust to a neutral position to relieve the twist.

16 Claims, 25 Drawing Sheets

Related U.S. Application Data continuation of application No. 29/580,596, filed on Oct. 11, 2016, now Pat. No. Des. 819,195, which is a continuation of application No. 29/565,482, filed on May 20, 2016, now Pat. No. Des. 796,667.

(60) Provisional application No. 62/424,589, filed on Nov. 21, 2016, provisional application No. 62/340,591, filed on May 24, 2016.

(51) Int. Cl.
 *A61B 1/005* (2006.01)
 *A61B 17/32* (2006.01)

(52) U.S. Cl.
 CPC .. *A61B 1/00135* (2013.01); *A61B 17/320068* (2013.01); *A61M 1/774* (2021.05); *A61B 1/0014* (2013.01); *A61B 1/00128* (2013.01); *A61B 2017/32007* (2017.08); *A61B 2017/320084* (2013.01); *A61B 2217/005* (2013.01); *A61B 2217/007* (2013.01)

(58) Field of Classification Search
 CPC ........ A61B 17/320068; A61B 1/00128; A61B 1/0014; A61B 2017/32007; A61B 2017/320084; A61B 2217/005; A61B 2217/007
 See application file for complete search history.

(56) References Cited

U.S. PATENT DOCUMENTS

| | | | |
|---|---|---|---|
| 4,425,115 A | | 1/1984 | Wuchinich |
| 4,516,398 A | | 5/1985 | Wuchinich |
| 4,634,419 A | | 1/1987 | Kreizman et al. |
| 4,734,964 A | | 4/1988 | Lane et al. |
| 4,747,820 A | | 5/1988 | Hornlein et al. |
| 4,750,902 A | | 6/1988 | Wuchinich et al. |
| 4,768,496 A | | 9/1988 | Kreizman et al. |
| 4,827,911 A | | 5/1989 | Broadwin et al. |
| 4,846,790 A | | 7/1989 | Hornlein et al. |
| 4,881,761 A | * | 11/1989 | Hornlein .................. A61M 1/85 285/332 |
| 4,921,476 A | | 5/1990 | Wuchinich |
| 4,931,047 A | | 6/1990 | Broadwin et al. |
| 4,978,333 A | | 12/1990 | Broadwin et al. |
| 4,988,334 A | * | 1/1991 | Hornlein ........ A61B 17/320068 601/2 |
| 5,015,227 A | | 5/1991 | Broadwin et al. |
| 5,162,044 A | * | 11/1992 | Gahn .................. A61F 9/00745 606/128 |
| 5,190,517 A | | 3/1993 | Zieve et al. |
| 5,221,282 A | | 6/1993 | Wuchinich |
| 5,421,829 A | | 6/1995 | Olichney et al. |
| 5,466,020 A | | 11/1995 | Page et al. |
| 5,484,398 A | | 1/1996 | Stoddard |
| D367,323 S | | 2/1996 | Carr |
| 5,492,528 A | | 2/1996 | Anis |
| 5,843,023 A | * | 12/1998 | Cecchi .................. A61B 17/435 604/44 |
| 5,984,904 A | | 11/1999 | Steen et al. |
| 6,083,191 A | | 7/2000 | Rose |
| 6,177,755 B1 | | 1/2001 | Hur |
| D438,952 S | | 3/2001 | Cimino et al. |
| 6,214,017 B1 | * | 4/2001 | Stoddard ........ A61B 17/320068 606/128 |
| 6,256,859 B1 | | 7/2001 | Stoddard et al. |
| 6,319,223 B1 | | 11/2001 | Wortrich |
| 6,468,059 B2 | | 10/2002 | Haser |
| 6,499,358 B1 | | 12/2002 | Hogan et al. |
| D477,867 S | | 7/2003 | O'Mahony |
| 6,595,957 B1 | | 7/2003 | Griffiths |
| 6,602,227 B1 | | 8/2003 | Cimino et al. |
| D479,320 S | | 9/2003 | O'Mahony |
| 6,654,999 B2 | | 12/2003 | Stoddard et al. |
| 6,723,110 B2 | | 4/2004 | Timm et al. |
| 7,204,825 B2 | | 4/2007 | Cimino et al. |
| D557,803 S | | 12/2007 | Muri |
| D557,804 S | | 12/2007 | Muri |
| 7,442,168 B2 | | 10/2008 | Novak et al. |
| 7,871,392 B2 | | 1/2011 | Sartor |
| 8,092,475 B2 | | 1/2012 | Cotter et al. |
| 8,118,823 B2 | | 2/2012 | Cotter et al. |
| 8,142,460 B2 | | 3/2012 | Cotter et al. |
| 8,211,103 B2 | | 7/2012 | Greep |
| D675,728 S | | 2/2013 | Tout |
| 8,518,066 B2 | | 8/2013 | Cotter et al. |
| D699,836 S | | 2/2014 | Burger |
| 9,149,291 B2 | | 10/2015 | Parham et al. |
| 9,421,027 B2 | | 8/2016 | Cotter et al. |
| 9,607,259 B2 | * | 3/2017 | Norman .................. B65D 23/14 |
| D796,667 S | | 9/2017 | Manandhar et al. |
| D819,195 S | | 5/2018 | Larsen et al. |
| 10,391,210 B2 | | 8/2019 | Manandhar et al. |
| 2002/0002369 A1 | | 1/2002 | Hood |
| 2003/0088235 A1 | * | 5/2003 | Tazi ..................... A61M 1/7411 604/542 |
| 2006/0052774 A1 | | 3/2006 | Garrison et al. |
| 2006/0063973 A1 | * | 3/2006 | Makower ............... A61B 1/233 600/114 |
| 2008/0200884 A1 | | 8/2008 | Perkins et al. |
| 2011/0160620 A1 | | 6/2011 | Gill et al. |
| 2014/0018732 A1 | * | 1/2014 | Bagaoisan ........ A61M 25/0136 604/95.04 |
| 2015/0080925 A1 | | 3/2015 | Schulte et al. |
| 2015/0328048 A1 | | 11/2015 | Koplin |
| 2017/0304655 A1 | | 10/2017 | Cotter et al. |
| 2017/0333606 A1 * | | 11/2017 | Manandhar ........ A61B 1/00131 |
| 2017/0354429 A1 | | 12/2017 | Ketelhohn et al. |

FOREIGN PATENT DOCUMENTS

| | | |
|---|---|---|
| JP | H0194841 A | 4/1989 |
| JP | H0199547 A | 4/1989 |
| WO | 9308750 A2 | 5/1993 |
| WO | 9517855 | 7/1995 |
| WO | 2004045705 | 6/2004 |
| WO | 2008154803 A1 | 12/2008 |
| WO | 2010057211 A1 | 5/2010 |
| WO | 2011005467 A2 | 1/2011 |
| WO | 2014134292 | 9/2014 |
| WO | 2015061258 | 4/2015 |
| WO | 2017187345 | 11/2017 |
| WO | 2017203408 | 11/2017 |

OTHER PUBLICATIONS

International Search Report and Written Opinion for PCT/IB2017/052980 dated Jul. 19, 2017.

International Search Report and Written Opinion for PCT/IB2017/053510 dated Nov. 13, 2017.

Partial Search Report for PCT/IB2017/053510 dated Sep. 22, 2017.

Franasiak, Jason M.; Ergonomic Strain in Minimally Invasive Surgery: Addressing the Strain Epidemic; www.jcomjournal.com; vol. 22, No. 6, pp. 267-273, Jun. 2015.

Krautkramer J. and Krautkramer H., Ultrasonic Testing of Materials, 1983.

Berguer, R.; Ergonomic problems associated with laparoscopic surgery; Surgical Endoscopy, 1999 13: 466-468; 1999.

Integra Lifesciences Corporation; CUSA Excel Ultrasonic Surgical Aspiration System, CUSA EXcel System User's Guide, 6 pages, 2007.

Integra Lifesciences Corporation; CUSA Excel+ Ultrasonic Surgical Aspirator, 8 pages, 2012.

SonaStar; Ultrasonic surgical aspiration system; Accuracy Matters, 2015.

Transmittal Letter of Related Cases dated Jan. 30, 2019.

Partial Search for International Application No. PCT/IB2017/057145 dated Jan. 31, 2018.

(56) References Cited

OTHER PUBLICATIONS

European Patent Office, International Search Report and Written Opinion for PCT/IB2017/057145 dated Mar. 15, 2018, dated Mar. 23, 2018, Rijswijk, NL.
IP Australia, Examination report No. 1 for application No. 2017271255 dated Mar. 3, 2021.

* cited by examiner

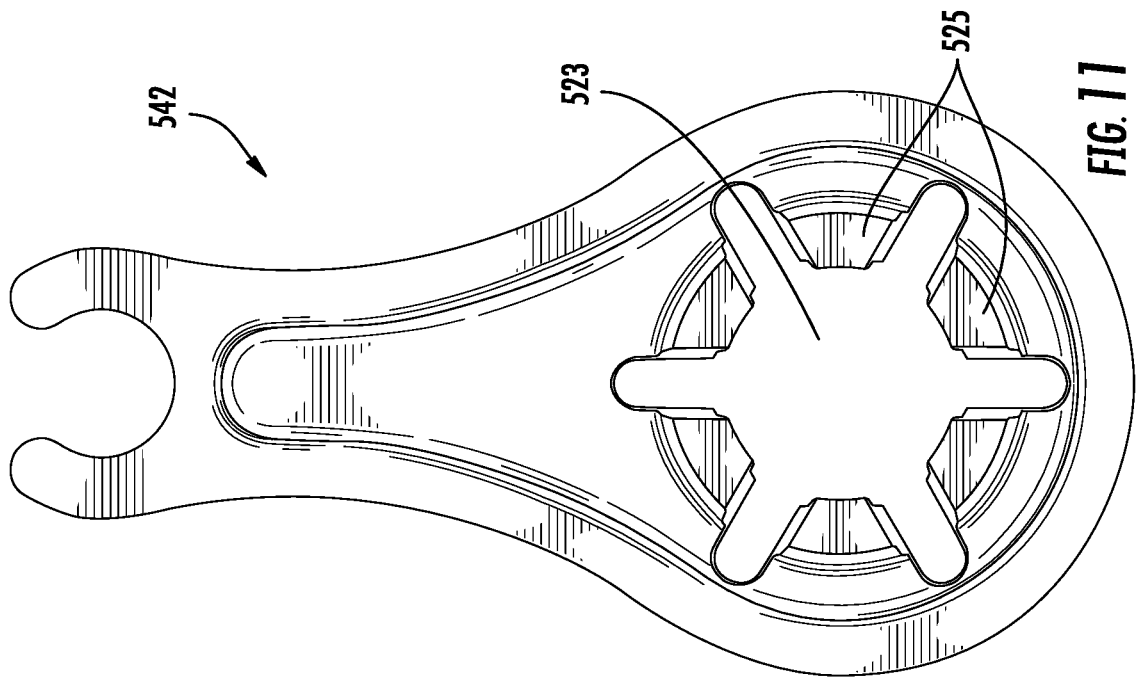
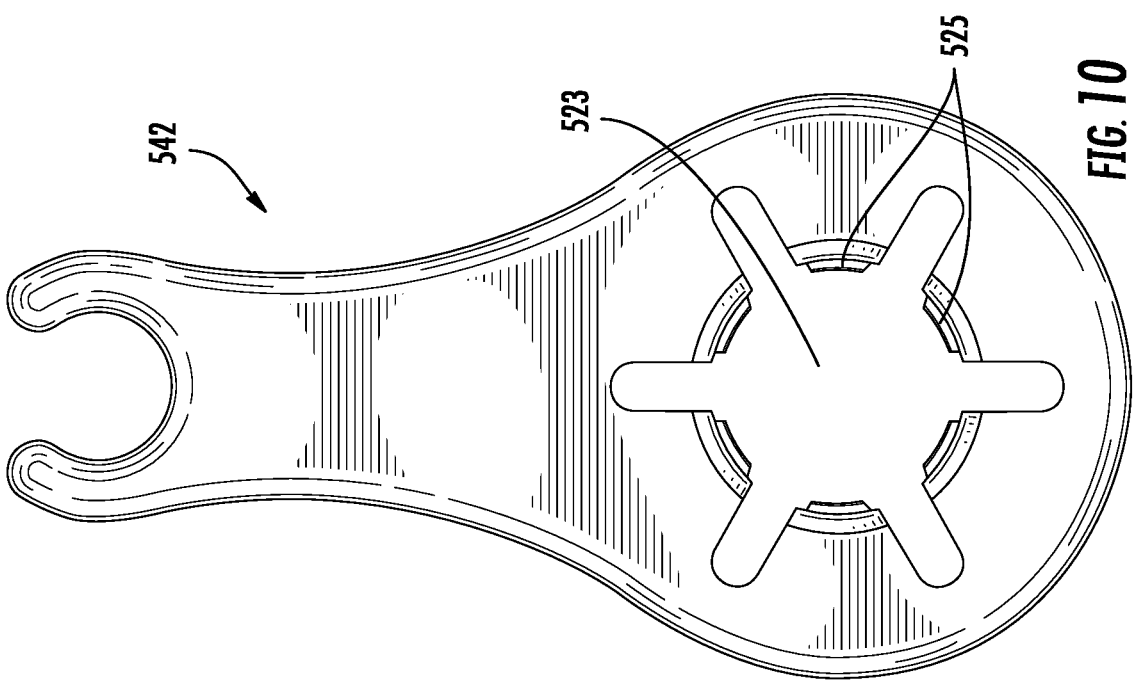

SECTION YZ-YZ

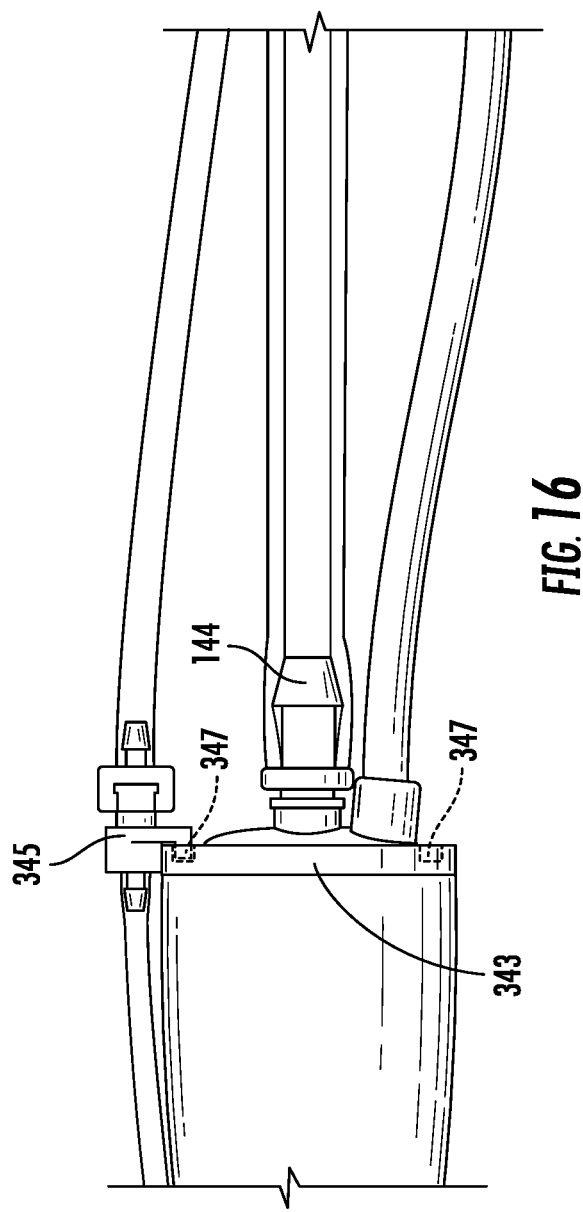

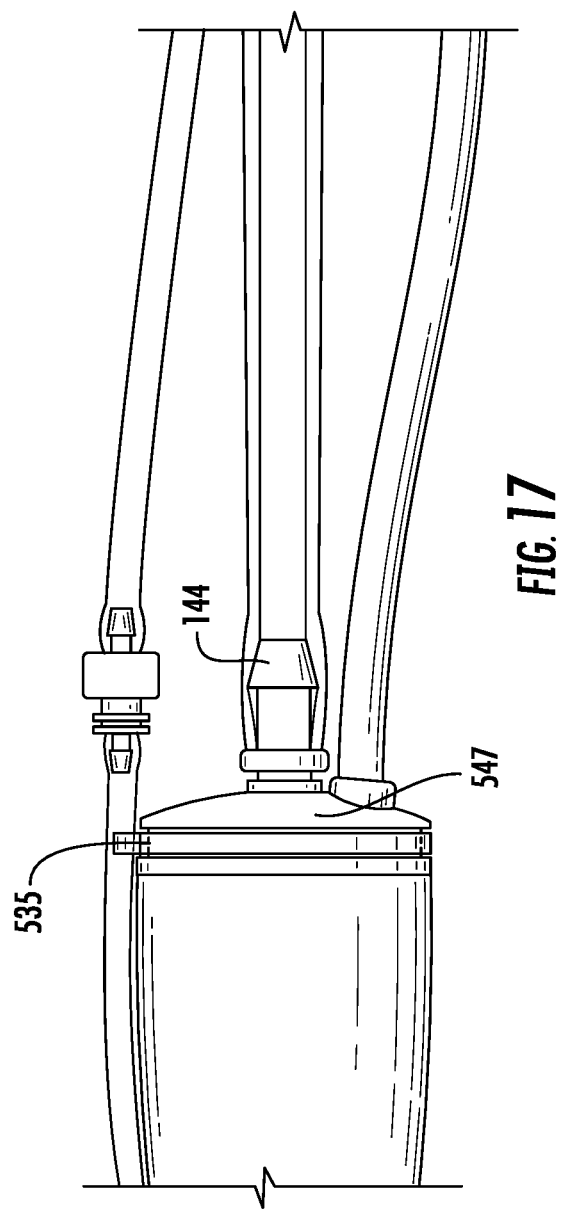

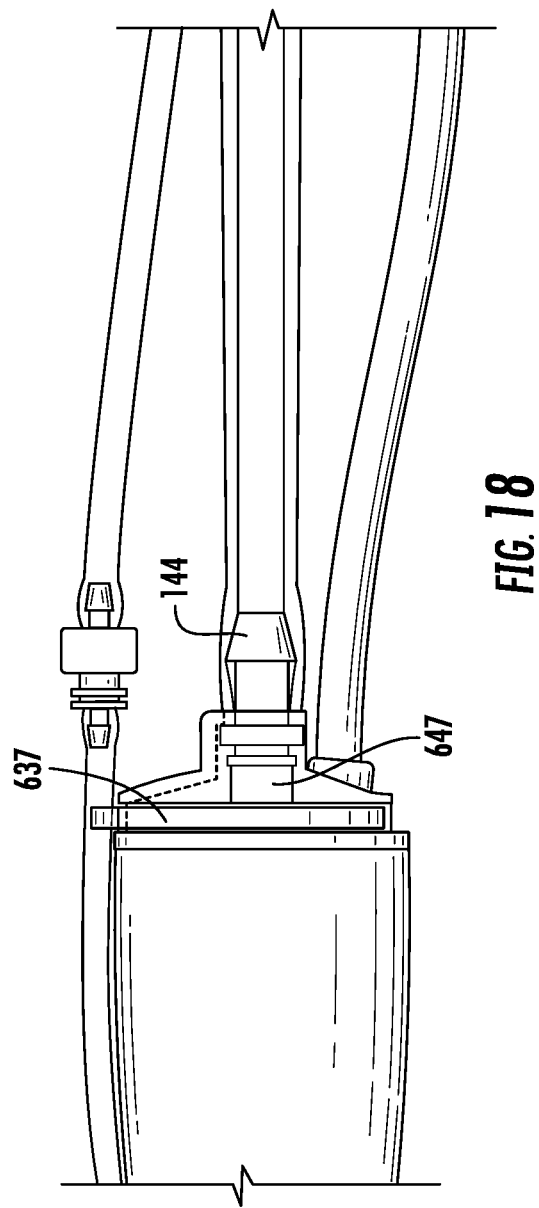

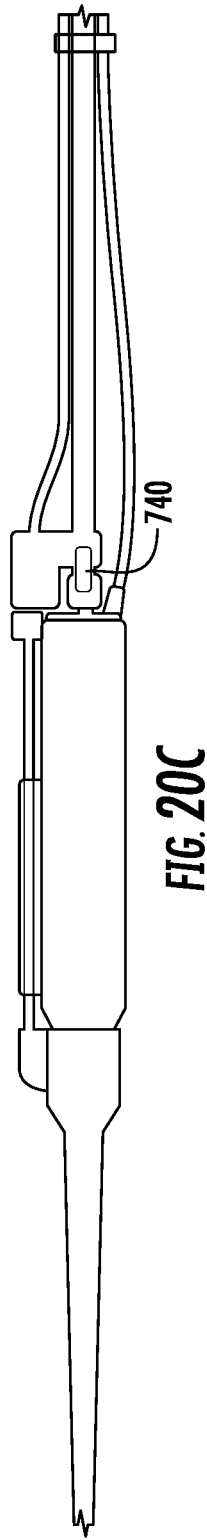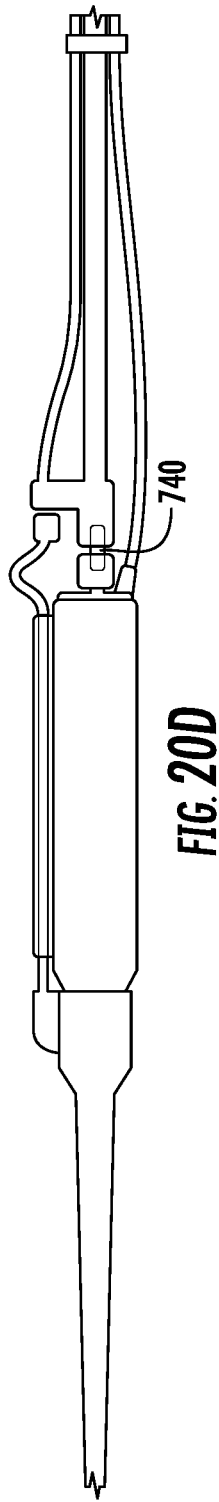

ERGONOMIC TUBING ATTACHMENT FOR MEDICAL APPARATUS

CROSS-REFERENCE TO RELATED APPLICATIONS

This application is a continuation of and claims priority and benefit under 35 U.S.C. § 120 to copending U.S. patent application Ser. No. 15/600,115, filed on May 19, 2017 which claims priority to and benefit under 35 U.S.C. § 119 to U.S. Provisional Application No. 62/424,589, filed Nov. 21, 2016 and U.S. Provisional Application No. 62/340,591, filed May 24, 2016, and also to U.S. Design application 29/565,482, filed May 20, 2016 and U.S. Design application 29/580,596, filed Oct. 11, 2016, the entire contents of each of which are hereby incorporated by reference.

BACKGROUND OF THE INVENTION

The embodiments of the present invention relate generally to tubing attachment mechanisms, and more particularly, to ergonomic tubing attachments for use in medical apparatus such as ultrasonic surgical aspirators.

Ultrasonic aspiration has become the standard of care for removal of tumors and diseased tissue in neurosurgery and general surgery. Ultrasonic aspirators are used for ultrasonic fragmentation of tissue at an operation site and aspiration of the tissue particles and fluid away from the site. Typically, ultrasonic surgical aspirators include an ultrasonic transducer supported within a handpiece, an ultrasonically vibrating horn or tip operably connected to the ultrasonic transducer, and a sleeve or flue positioned about the horn. The horn includes a longitudinally extending central bore having one end located adjacent a distal tip and a second end located adjacent the proximal end of the horn. The proximal end of the horn is adapted to engage a vacuum source to facilitate aspiration of fluid. The flue is positioned about the horn to define an annular passage. Irrigation fluid is supplied through the annular passage around the horn to the surgical site where it mixes with blood and tissue particles and is aspirated through the bore in the horn. By mixing the irrigation fluid with the blood and tissue particles, coagulation of the blood is slowed down and aspiration thereof is aided. When the longitudinally vibrating tip in such an aspirator is brought into contact with tissue, it gently, selectively, and precisely fragments and removes the tissue. U.S. Pat. Nos. 5,015,227 and 4,988,334 disclose such ultrasonic surgical devices and are incorporated herein by reference. A known ultrasonic aspirator on the market is the CUSA EXcel® Ultrasonic Surgical Aspirator (Integra Life-Sciences Corporation, Plainsboro, N.J., U.S.A.).

Surgeons frequently need to use surgical instruments, such as handpieces in ultrasonic aspirator systems, for long periods of time while maintaining dexterity. A "pencil-grip" is often employed for precise handling. This style of gripping a long thin object is also known as the "dynamic tripod grip" in the biomechanics literature. During precise manipulation of the instrument, a complex set of antagonistic muscles are employed in the human hand to control shaking and maintain the desired trajectory of the surgical instrument.

The energy stored in twisting an elastomeric tube can be quite large. For example, a toy aircraft can be powered by the energy stored in the twist of an elastic band for up to several minutes on a single winding. In the case of the surgical handpiece, due to the length of the tubing going from the handpiece to the instrument console or wall vacuum outlet, the elastic energy stored in the tubing can be large even for small twist angles. Also, as the tubing is handed over from the assistant to the surgeon or between multiple surgeons operating simultaneously, the tubing can get progressively wound up requiring the surgeon to provide more and more opposing force to keep the tool tip from rotating. If a dynamic mechanism to alleviate the torque is not provided, the ergonomic situation can get progressively worse. The length of tubing that is not directly used can be coiled and placed in the vicinity of the surgical field. The act of coiling and uncoiling can also build up twist.

In recent years, the surgical community has gradually moved from open surgery to laparoscopic surgery (also known as Minimally Invasive Surgery or MIS) for certain surgical procedures. In this modality of surgery, the grip style of surgical instruments is slightly different
it is more like grasping a screwdriver, rather than a pencil-like grip. In this style of grip, the rotation or torque of the instrument is even more prominent than in the pencil-like grip.

The fact that ergonomics of existing instruments are poor has been documented by surgeons. For example, Berguer et al. have observed that surgeons reported increased upper-extremity fatigue and occasional hand numbness after laparoscopic procedures (Surgical Endoscopy (1999) 13: 466-468). Franasiak and Gehrig have reported that recent data on MIS surgeons indicate very high rates of surgeon strain, 88% when robotic assistance is not used, and identify instrument design as a major concern (J. of Clinical Outcomes Management (2015) 22(6): 267-273).

There are many different parameters that confound the factors that can be studied in attempting to design surgical instruments and tubing attachments to alleviate surgeon fatigue in prolonged use. Attempts have been made, for example, by reducing the stiffness of the tubing while maintaining non-kinkability, or by keeping the flexibility of the tubing while keeping the stiffness high.

U.S. Pat. No. 8,211,103 discloses an electrosurgical instrument with an adjustable power cable. The electrosurgical instrument includes a hand piece that is connected to an electrosurgical generator by way of an electrical cable. The hand piece includes a channel system that receives a portion of the electrical cable therein and allows a physician to adjust the location on the hand piece at which the electrical cable exits the hand piece.

U.S. Patent Application Publication No. 2008/0200884A1 describes an ophthalmic surgical instrument that includes a reinforcement structure, such as ribs, on the outer surface of the irrigation tubing to resist kinking of the tubing during surgery.

However, prior art does not recognize that a significant portion of the fatigue is due to the rotational twist of the tubing. Prior art has failed to identify this major factor associated with surgical instruments that adds to the surgeon fatigue problem and has not provided satisfactory solutions.

Hence, those skilled in the art have recognized a need for ergonomic surgical instruments that alleviate surgeon fatigue in prolonged use. The embodiments of the present invention fulfill this need and others.

SUMMARY OF THE INVENTION

It has been identified that a significant portion of surgeon fatigue in prolonged use of surgical instruments is due to the rotational twist of the tubing. The torque of the tubing attachments provides a resistance to rotation that the surgeon has to continuously oppose. An advantage of this invention is the elimination of such twist.

Briefly and in general terms, some embodiments of the present invention provide mechanisms in a tubing attachment joint design to dynamically neutralize this twist. The first mechanism is a molded swivel joint that can be snapped into a groove of a luer device. The swivel extends out from the center where a cradle is provided to capture one tube. This geometry allows the tubing to rotate without twisting eliminating the need for surgeons to resist twist. The second mechanism is the paired choice of materials and geometric tolerances between the tubing inner diameter and a male luer fitting. The design is such that vacuum leaks are not formed while the tubing can rotate in the joint with very little application of rotational moment. Thus the twist in the vacuum tubing can be eliminated regardless of coiling of the remaining length of the tubing.

In some embodiments of the invention, for example, a tubing attachment system for use in a medical apparatus having a handpiece and a tube to be connected proximally to the handpiece may comprise a tubing attachment component having a proximal end, a distal end and an external surface. In some embodiments, the tubing attachment component may comprise a proximal end portion configured to attach to the tube, a distal end portion configured to attach to the handpiece, a throughbore extending from the distal end to the proximal end, and a circumferential groove on the external surface between the proximal end portion and the distal end portion. In various embodiments, the tubing attachment may include a capture component comprising a frame that has an internal frame surface, an external frame surface, and a frame opening for receiving the tubing attachment component. Moreover, in some embodiments, the frame may comprise at least one locking protrusion extending inward from the internal frame surface. In various embodiments, the frame and the at least one locking protrusion may be configured to fit in the circumferential groove and may be rotatable in the circumferential groove about the tubing attachment component when an external force is applied and to frictionally lock the tubing attachment component in a desired rotational position in the absence of such external force.

In addition, in various embodiments, the capture component may have at least three of the locking protrusions disposed on the internal frame surface of the frame with contact surfaces facing inward. In various embodiments, the external force may be intentionally applied by a user to rotate the frame about the tubing attachment component, or is caused by coiling of the tube attached to the proximal end portion of the tubing attachment component. Moreover, in various embodiments, the coiling of the tube may produce the external force, which causes the capture component to rotate about the tubing attachment component whereby the tubing attachment system self-adjusts to a neutral position to relieve the coiling of the tube. In some embodiments, the proximal end portion may comprise a conical body transitioning into a radially outwardly extending barb for securing the tube, and the distal end portion may comprise a fitting for engaging a corresponding fitting on the handpiece. In various embodiments, the tubing attachment component may comprise a flange between the conical body and the fitting, and the flange may form a rail of the circumferential groove. Moreover, in some embodiments, the capture component may comprise a pair of arms extending outwardly from the external frame surface forming a channel for holding another tube. In various embodiments, the tubing attachment system is in combination with a medical apparatus. Moreover, in some embodiments, the medical apparatus may be an ultrasonic surgical apparatus.

In some embodiments, a medical apparatus may include a handpiece and a tube. Moreover, in various embodiments, the tube may be connected to the handpiece through a swivel joint which allows the tube to rotate circumferentially with respect to the handpiece without axial displacement of the tube.

In addition, in various embodiments, the swivel joint may include a tubing attachment component comprising a longitudinal throughbore and a circumferential groove on an external frame surface. In some embodiments, the swivel joint may include a capture component comprising a frame with a frame opening and at least one locking protrusion extending inward from an internal frame surface of the frame. Moreover, in some embodiments, the frame may be snapped into the circumferential groove of the tubing attachment component and rotate about the tubing attachment component. In various embodiments, the at least one locking protrusion may allow the capture component and tubing attachment component to be fixed at a desired relative position. In some embodiments, the capture component may have at least three locking protrusions extending radially inward from the internal frame surface of the frame. Moreover, in various embodiments, the tubing attachment component may further comprise a flange extending from the external frame surface of the tubing attachment component. In some embodiments, the capture component may comprise a pair of arms extending outwardly from the external frame surface forming a channel for holding another tube. In some embodiments, the swivel joint may allow the tube, when twisted, to self-adjust to a neutral position to relieve the twist of the tube. In various embodiments, the medical apparatus may be an ultrasonic surgical apparatus. In addition in some embodiments, the tube may be an irrigation tube or an aspiration tube.

In various embodiments, a tubing attachment system for use with an ultrasonic surgical apparatus having a handpiece and an aspiration tube to be connected proximally to the handpiece, wherein the tubing attachment system may comprise a tubing attachment component. The tubing attachment component may comprise a longitudinal throughbore and a circumferential groove on an external frame surface. In some embodiments, the tubing attachment component may comprise a proximal end portion configured to attach to the aspiration tube and a distal end portion configured to attach to the handpiece. In some embodiments, the tubing attachment system may include a capture component comprising a frame having a front side and an opposing back side and a longitudinal frame opening extending between the front side and the back side. In various embodiments, the longitudinal frame opening may be defined by a plurality of locking protrusions, each locking protrusion may have a proximal end and a distal free end, wherein the proximal end projects from the frame adjacent the front side and the distal free end adjacent the back side. In some embodiments, each locking protrusion may narrow the longitudinal frame opening from the front side to the back side. Moreover, in some embodiments, the frame between the front side of the frame and the distal free ends of the plurality of locking protrusions may be longitudinally held between the longitudinal extent of the circumferential groove of the tubing attachment component while allowing rotation of the capture component about the tubing attachment component. In various embodiments, the plurality of locking protrusions may allow the capture component to rotate about the tubing attachment component when a threshold external force is applied to the tubing attachment component.

In addition, in various embodiments, the capture component may further comprise a channel at a radial position away from the longitudinal frame opening for holding one or more tubes. In some embodiments, the tubing attachment system may be in combination with an ultrasonic surgical apparatus that has a handpiece and an aspiration tube connected to the proximal end portion of the tubing attachment component. In various embodiments, the tubing attachment component may further comprise at least one flange extending from the external frame surface of the tubing attachment component to define the longitudinal extent of the circumferential groove. In some embodiments, each of the locking protrusions include contact surfaces facing inwardly that extend from the proximal end to the distal free end of the locking protrusion.

In accordance with aspects of the invention, there is provided a tubing attachment system for use in a medical apparatus having a handpiece and a tube to be connected proximally to the handpiece. The tubing attachment system comprises a tubing attachment component and a capture component. The tubing attachment component has a proximal end, a distal end and an external surface, and comprises a proximal end portion configured to attach to the tube, a distal end portion configured to attach to the handpiece, a throughbore extending from the distal end to the proximal end, and a circumferential groove on the external surface between the proximal end portion and the distal end portion. The capture component comprises a frame having an internal frame surface, an external frame surface, and a frame opening for receiving the tubing attachment component, the frame comprising at least one locking protrusion extending inward from the internal frame surface. The frame and the at least one locking protrusion are configured to fit in the circumferential groove and be rotatable in the circumferential groove about the tubing attachment component when an external force is applied and to frictionally lock the tubing attachment component in a desired position in the absence of such external force. There may be two or at least three locking protrusions extending radially inward from an internal surface of the frame. The external force may be intentionally applied by a user to rotate the frame about the tubing attachment component, or may be caused by coiling of the tube attached to the proximal end portion of the tubing attachment component. The external force required to rotate the frame may be predetermined or adjusted based on the friction provided by the locking protrusions. For example, the external force required may be very low so that the system can self-adjust to a neutral position to relieve tubing twist.

In more detailed aspects, the proximal end portion comprises a conical body transitioning into a radially outwardly extending barb for securing the tube, and the distal end portion comprises a fitting for engaging a corresponding fitting on the handpiece.

In accordance with other aspects of the invention, there is provided a medical apparatus comprising a handpiece and a tube, wherein the tube is connected to the handpiece through a swivel joint which allows the tube to rotate circumferentially with respect to the handpiece without axial displacement of the tube. The swivel joint may comprise a tubing attachment component comprising a longitudinal throughbore and a circumferential groove on its external surface; a capture component comprising a frame with a frame opening and locking protrusions extending radially inward from an internal surface of the frame; wherein the frame can be snapped into the circumferential groove of the tubing attachment component and rotate about the tubing attachment component; and wherein the locking protrusions allow the capture component and tubing attachment component to be fixed at a desired relative position.

In further detailed aspects, the tubing attachment component may further comprise a flange, for example an annular flange, between the conical body and the fitting, and the flange may form or serve as a rail of the circumferential groove. The capture component may further comprise a pair of arms extending outwardly from the external frame surface forming a channel for holding another tube. The arms may be a pair of curved arms forming an inward facing channel for receiving a tube. Additional arms may be provided, extending from the external frame surface or from an arm, to hold one or more additional tubes, wires or accessories.

Other features and advantages of the embodiments of the present invention will become more apparent from the following detailed description of the invention, when taken in conjunction with the accompanying exemplary drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

Embodiments of the presently disclosed shear stress ultrasonic horn are described herein with reference to the drawings, in which:

FIG. 10 is a front elevational view of the capture component of FIG. 8;

FIG. 11 is a rear elevational view of the capture component of FIG. 8;

FIG. 16 illustrates an embodiment of a tubing attachment component assembled in a medical apparatus and other tubing connectors;

FIG. 17 illustrates further embodiments of a tubing attachment component and a capture component assembled in a medical apparatus;

FIG. 18 illustrates the tubing attachment component and capture component shown in FIG. 17 with a different rear cap component in the assembly;

FIGS. 20A, 20B, 20C, 20D, and 20E illustrate additional alternative embodiments of tubing connection architectures;

DETAILED DESCRIPTION OF THE PREFERRED EMBODIMENTS

Figure 1:
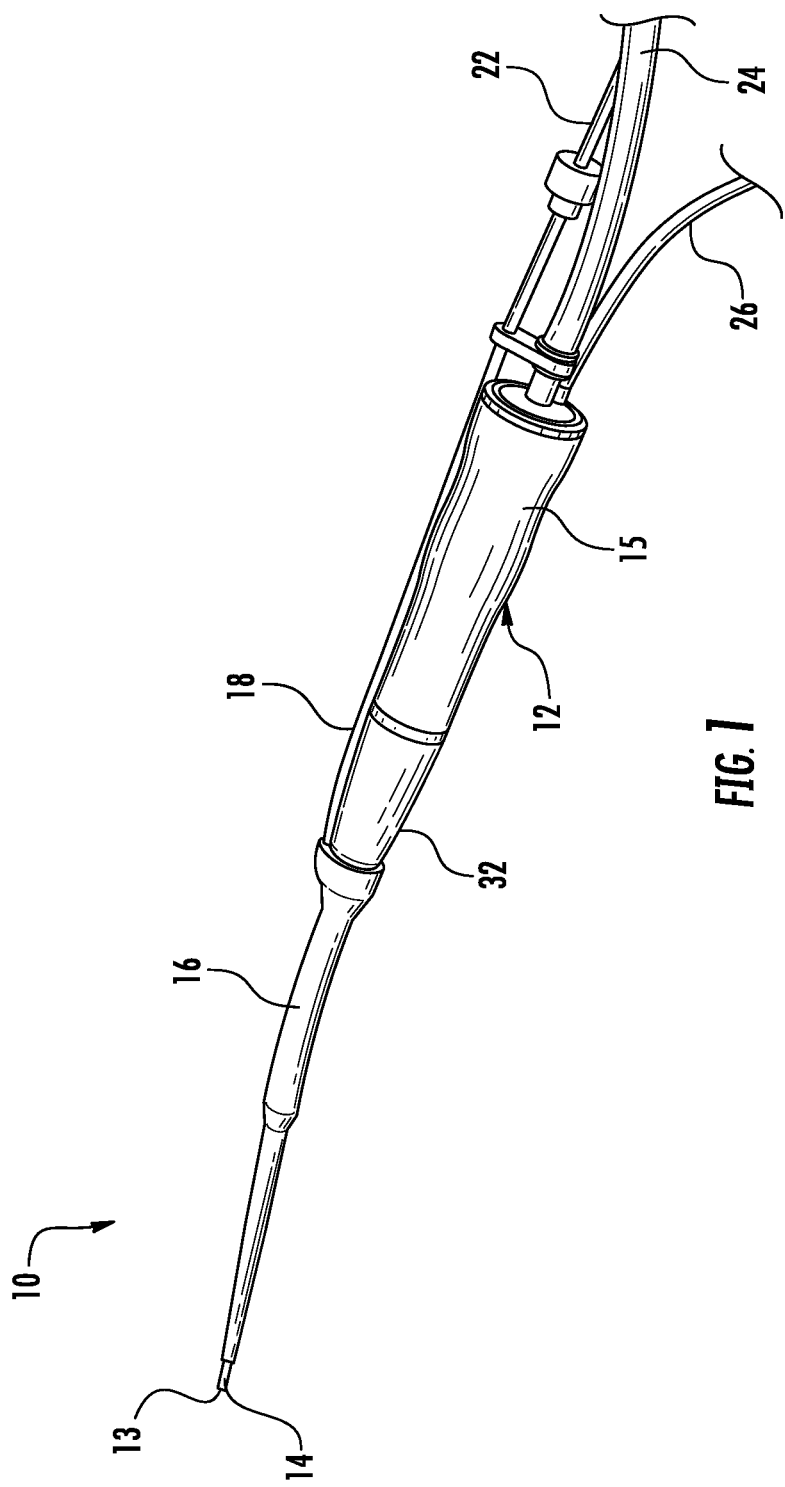
FIG. 1 is a perspective view of an ultrasonic apparatus in accordance with an embodiment of the present invention.
Figure 2:
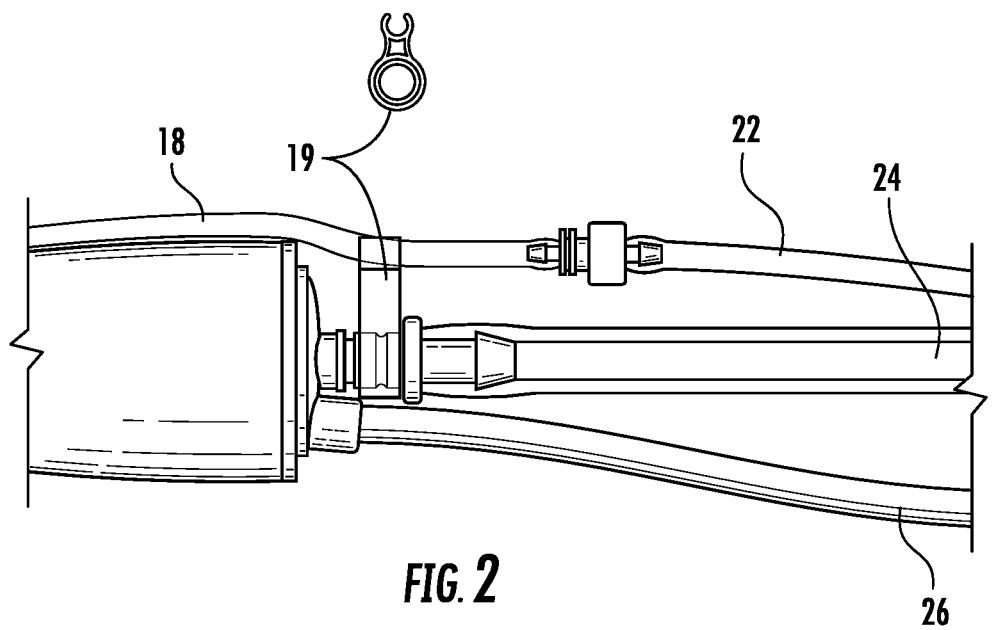
FIG. 2 illustrates the proximal end of the apparatus of FIG. 1 in more detail and additionally includes a detailed view of the capture component.
Figure 3:
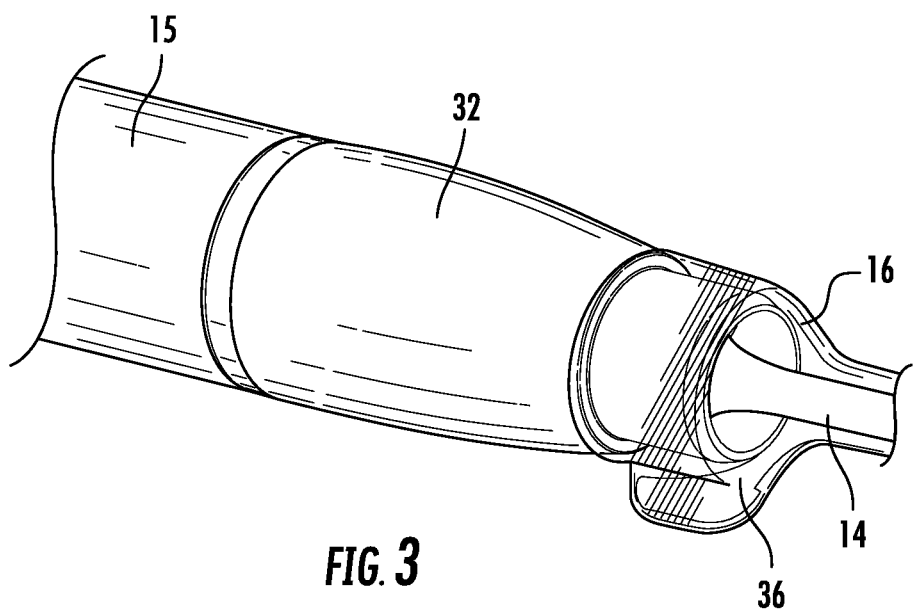
FIG. 3 is a perspective view a nosecone fully assembled to a handpiece and supporting the flue (the flue or flue tube is not shown in this drawing)
Figure 4:
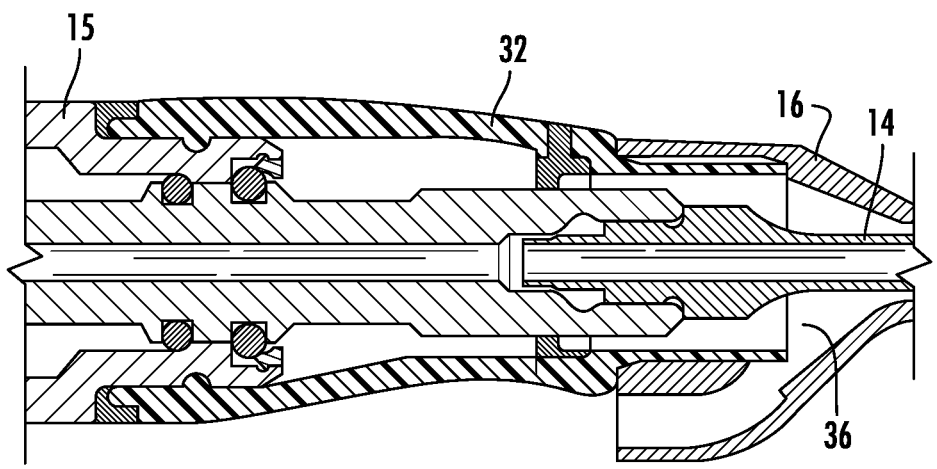
FIG. 4 is a cross-sectional view of a portion of the ultrasonic apparatus of FIG. 1.

Embodiments of the presently disclosed tubing attachment system will now be described in detail with reference to the drawings, in which like reference numerals designate identical or corresponding elements in each of the several views. As used herein, the term "distal" refers to that portion of the instrument, or component thereof which is farther from the user while the term "proximal" refers to that portion of the instrument or component thereof which is closer to the user during normal use. The terms "ultrasonic horn," "ultrasonic tip," "ultrasonic aspirating tip," "ultrasonic surgical aspirating tip," "aspirating tip," "ultrasonic surgical tip," "surgical tip", "horn" and "tip" are used herein interchangeably. The terms "tube" and "tubing" are used herein interchangeably. The terms "capture component," "tube clip," "tubing clip," "flue tube clip," "flue tubing clip," "flue irrigation tube clip," and "flue irrigation tubing clip" are used herein interchangeably.

It has been found that precise pronation and supination or rotating during pencil grip is an aspect of tool handling that results in greater fatigue in surgeons than other manipulations such as changing the yaw or pitch of the instrument orientation. This could be because of the need to use weaker finger muscles to rotate an instrument, while other movements can leverage the larger wrist muscles. It has also been identified that the torque of the tubing attachments provides a resistance to rotation that the surgeon has to continuously oppose. The fatigue in rotational movement is often accentuated by the presence of cables and tubing attachments present in electromechanical surgical instruments.

Three sets of attachments are usually present in the ultrasonic surgical apparatus—irrigation tubing to supply irrigant to surgical site, aspiration tubing to provide suction, and electrical wires to power the instrument or provide switching connections. A particularly objectionable aspect of these attachments is the torque provided by the twisting of the tubing and cables, which the surgeon has to constantly overcome to maintain precise trajectory of the instrument. In electromechanical surgical handpieces, the torque due to the torsional twisting of tubing and cable attachments has been identified in an embodiment of the present invention as a major contributor to surgeon fatigue.

Referring now to FIGS. 1-4, one embodiment of the presently disclosed apparatus for ultrasonically fragmenting and aspirating tissue is shown. Generally an ultrasonic surgical apparatus 10 includes a handpiece 12 for use by a surgeon to direct fragmentation. The handpiece 12 encases a transducer (not shown) on which a surgical tip or ultrasonic horn 14 is fastened. The ultrasonic horn can be powered by the transducer and be ultrasonically actuated to fragment tissue and suction effluent via a central channel. A distal end portion 13 of the ultrasonic horn 14 extends beyond a distal end of the flue 16. Ultrasonic horn 14 is vibrated to fragment tissue during surgery. The ultrasonic horn may be made of titanium or other conventional materials known in the art.

A cooling and irrigation system which provides cooling fluid to the ultrasonic horn 14 is provided for maintaining temperature within an acceptable range. The handpiece 12 includes a housing 15, which may be formed of a sterilizable plastic, metal or other suitable materials or a combination thereof. The flue 16 provides a path for irrigation fluid or liquid and connects to the distal end of the housing 15. The flue 16 typically connects to the handpiece 12 via a nosecone 32. The flue 16 may include or attach to a flue tube 18. The nosecone 32 connects to the handpiece 12 and covers the internal portion of the ultrasonic horn 14.

An irrigation tube 22 connects to the flue tube 18 upstream and supplies irrigation fluid through the flue tube 18 to an operative site during surgery. An aspiration tube 24 provides suction and a path for aspiration from the operative site to a collection canister (not shown). Alternatively, the aspiration tube may be mounted outside of the housing 15. A flue tube clip or capture component 19 allows for adjustment of the location of the flue tube 18 per the desires of the surgeon during operation. An electrical cable 26 provides power to the apparatus or provides switching connections.

Figure 5:
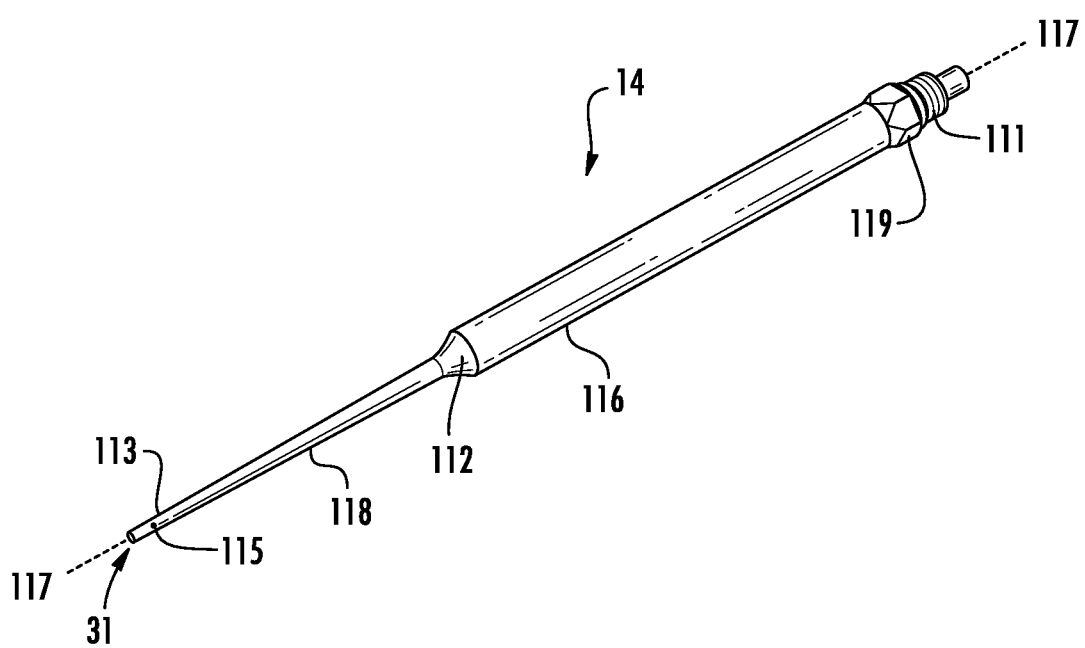
FIG. 5 is a perspective view of an ultrasonic horn.
Figure 6A:
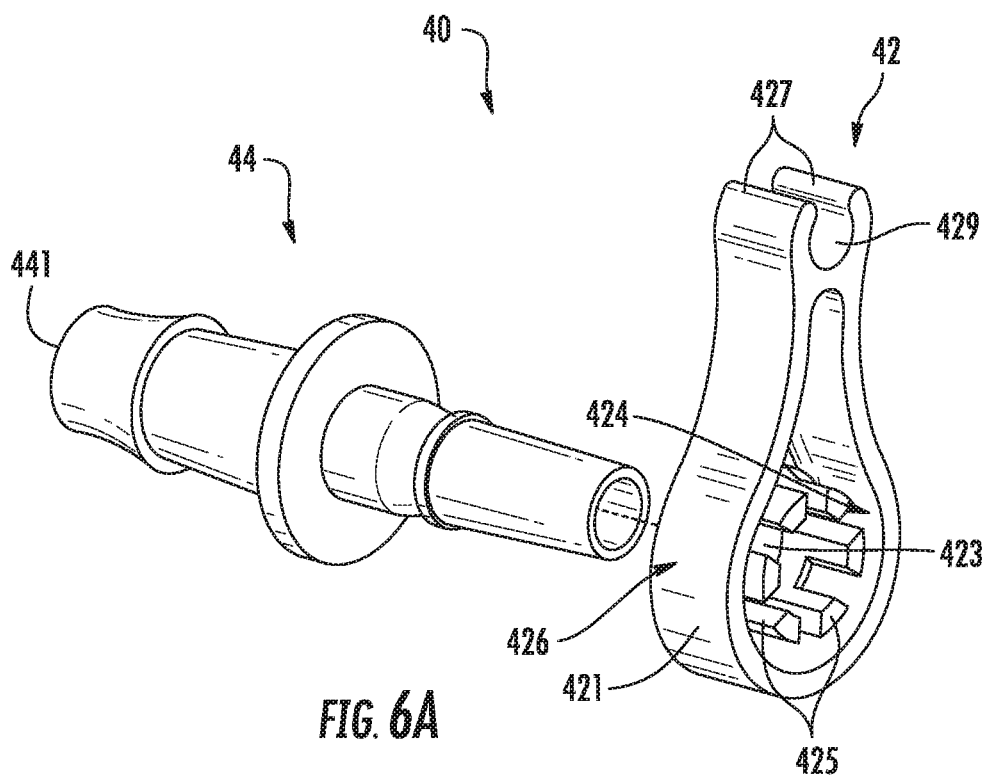
FIG. 6A illustrates a tubing attachment system of an embodiment of the present invention in a dissembled state.
Figure 6B:
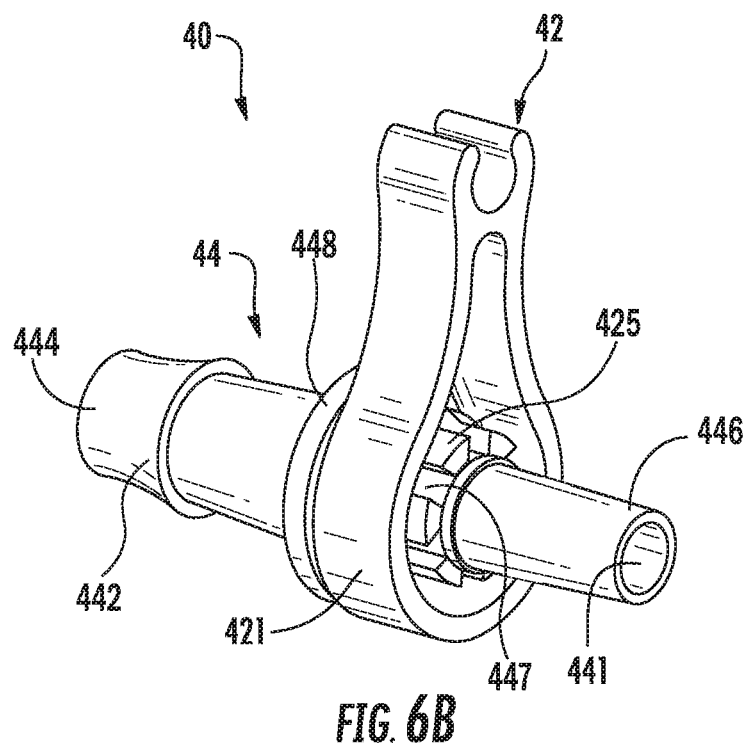
FIG. 6B illustrates the tubing attachment system of FIG. 6A in an assembled state.
Figure 7A:
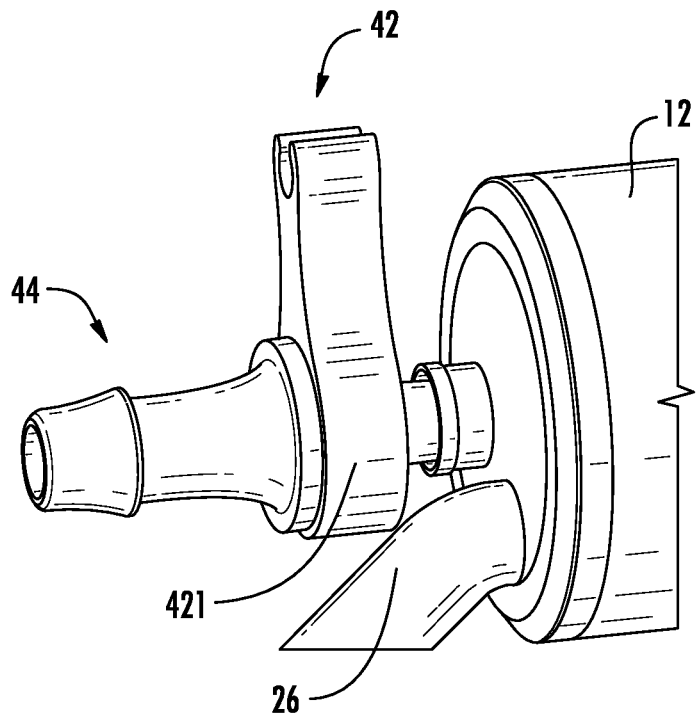
FIG. 7A illustrates the tubing attachment system of FIG. 6A and a handpiece in a assembled state.
Figure 7B:
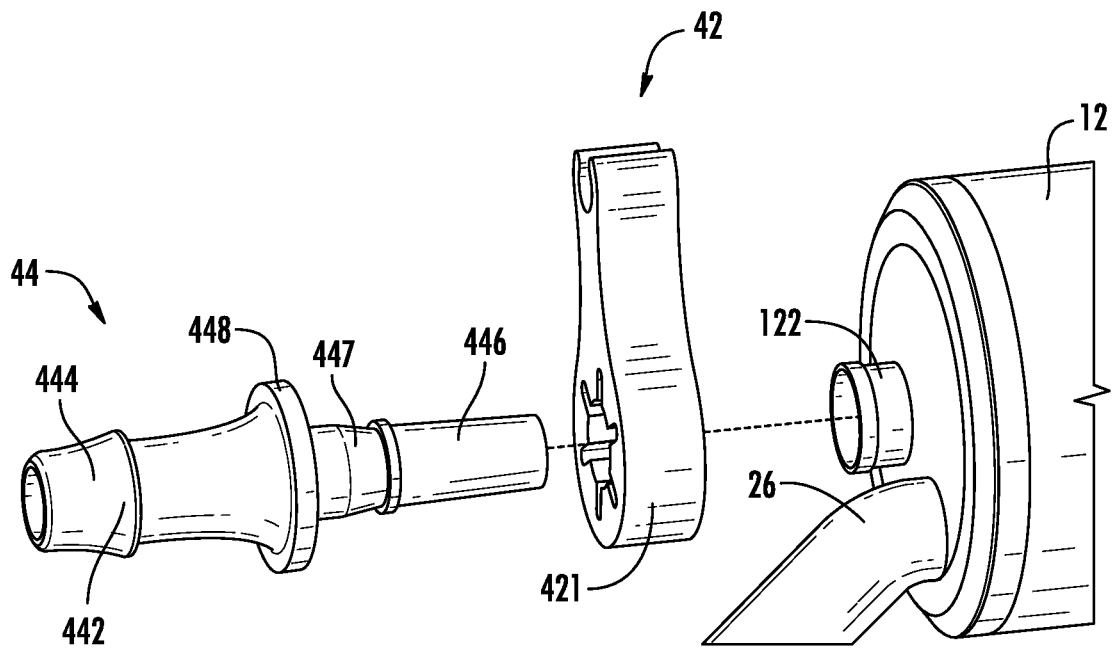
FIG. 7B illustrates the elements shown in FIG. 7A in a disassembled state.
Figure 8:
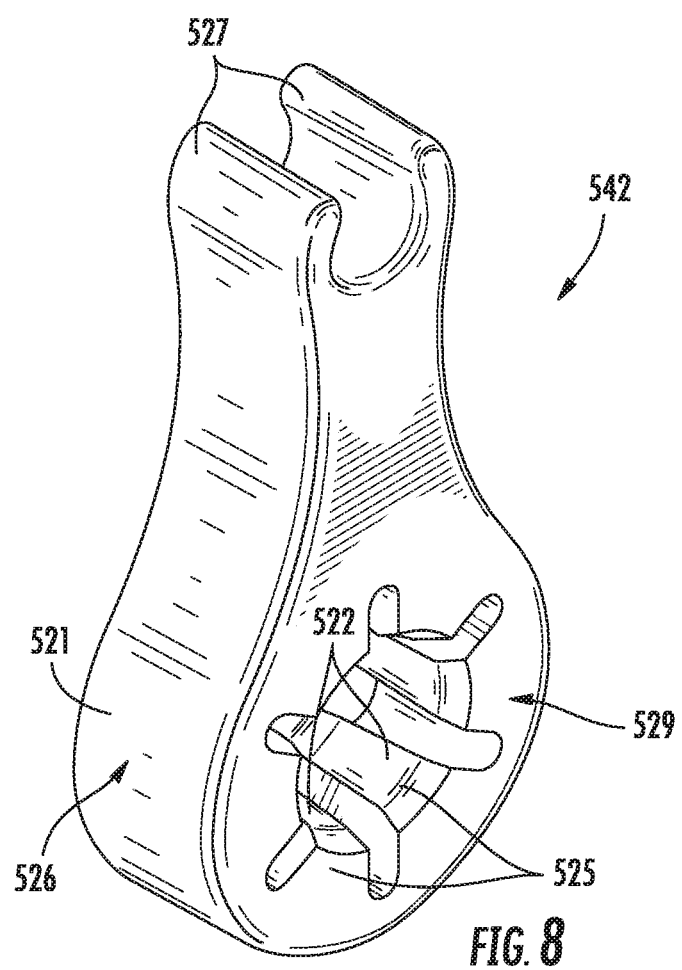
FIG. 8 is a front perspective view of a capture component in accordance with an embodiment of the present invention.
Figure 9:
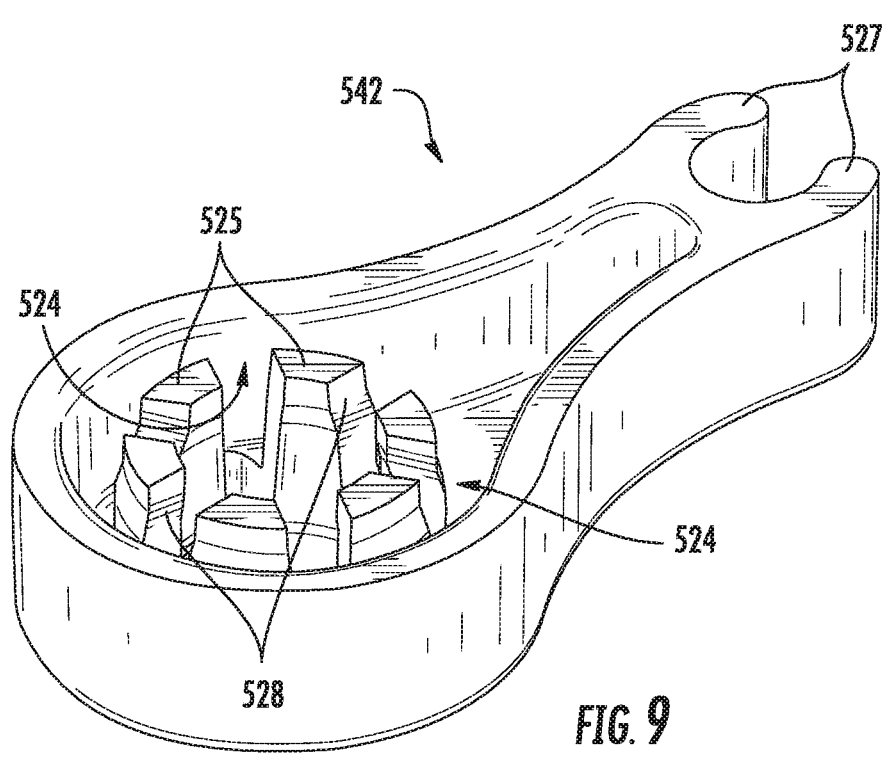
FIG. 9 is a rear perspective view of the capture component of FIG. 8.

FIG. 5 illustrates an embodiment of an ultrasonic tip or ultrasonic horn 14, which is suitable for use with the above-described ultrasonic surgical apparatus for fragmenting and aspirating tissue. The ultrasonic horn includes a first horn extender 116 and a second horn extender 118 extending distally from the first horn extender through a horn extender transition segment 112. The ultrasonic horn 14 may have a third horn extender and additional horn extenders. The ultrasonic horn has a distal end portion 113 and a threaded proximal end 111, a throughbore 117, a preaspiration hole or transverse bore 115, and a hexagon engagement portion 119. The ultrasonic horn has a larger diameter in the first horn extender 116 section and a smaller diameter in the second horn extender 118 section. Although the ultrasonic horn as shown is a stepped horn, it is known that there are ultrasonic horns that are not stepped. For example, the ultrasonic horns can have a single long extender, rather than two diameters, and the single long extender can have a constant diameter throughout its length or have a gradually changing diameter along its length, for example, gradually decreasing in diameter along its length distally. In addition, even though two extenders may form a stepped configuration, additional extender or extenders may form additional steps or transition smoothly from another extender without forming any apparent step. The ultrasonic horn may vibrate in the ultrasonic frequency range with a longitudinal amplitude in excess of about 5 mils (0.005 inch) to 14 mils (0.014 inch).

The ultrasonic horn 14 is substantially circular and disposed within the flue 16. During operation of the ultrasonic apparatus 10, irrigation fluid is supplied through the irrigation tube 22 and flue tube 18 into the flue 16. The flue 16 and the ultrasonic horn 14 define an annular cavity 36 therebetween. Irrigation fluid is supplied from flue 16 through cavity 36 to the distal end of the ultrasonic horn 14. A transverse bore is formed in preaspiration holes 115 near the distal end of the ultrasonic horn 14 and communicates with the throughbore 117. The irrigation fluid is drawn from preaspiration holes 115 and the surgical site into inlet 31 of the throughbore 117 along with fragmented tissue, blood, etc., and is removed from the surgical site via the throughbore 117 and the aspiration tube 24. The transverse bore provides an alternate route for fluid to enter throughbore 117 when inlet 31 becomes clogged.

In a more detailed aspect, irrigation liquid, for example saline, is necessary to cool the surgical tip and site of tissue fragmentation. This irrigation liquid is provided to the flue with a peristaltic pump at a rate as low as 2 to 3 ml/min, which is only typically about a drip or two a second. The irrigation liquid is supplied at the proximal end of the ultrasonic horn. The irrigation liquid progresses to near the distal end of the ultrasonic horn, where two preaspiration holes, which may each have a 0.015 inch diameter for example, suction a majority, perhaps 90-95%, of the irrigation through the holes connecting the outside horn diameter to the central suction channel. This action of irrigation and suction supports a contiguous cooling circuit for the vibrating titanium metal and it also helps to wet effluent such as blood and tissue in the central channel. Some irrigation is also favorable to cooling the surgical site, improving coupling to tissue, and affording cavitation necessary to emulsification and aspiration of tissue, such as tumors.

Referring now to FIGS. 6A, 6B, 7A and 7B, a swivel joint or tubing attachment system 40 comprises a tubing clip or capture component 42 and a tubing attachment component 44. The capture component 42 comprising a frame 421 having a frame opening 423 that allows a tube or the tubing attachment component 44 to go through. The frame 421 has locking protrusions (or locking teeth or fingers) 425 that hold or grip the tube or tubing attachment component in a desired position. The locking protrusions may be extending radially inward from an internal frame surface 424 of the frame 421. The tubing capture component 42 also has two arms 427 that extend from the frame 421 and are able to hold another tube, such as the flue tube or irrigation tube, a cable or other accessory in a desired position relative to the aspiration tube or suction tube. The two arms 427 may be curved towards each other, forming a channel 429 allowing a tube, cable or accessory to be retained, inserted and/or retained between the two arms. The capture component 42 allows a user to clock the flue tube at any position as desired. One or more additional arms may be provided, extending from an external frame surface 426 or from an arm 427, to hold one or more additional tubes, cables or accessories.

The frame 421 and locking protrusions 425 are configured to fit in the circumferential groove 447. The capture component 42 may be snapped onto an extended section of the tubing attachment component 44 allowing rotation to neutralize torque. For example, the frame 421 can be snapped into the circumferential groove 447 of the tubing attachment component 44 and rotate about the tubing attachment component 44 when an external force is applied and to frictionally lock the tubing attachment component in a desired position in the absence of such external force. The external force may be intentionally applied by a user to rotate the frame about the tubing attachment component, or may be caused by coiling of the tube attached to the proximal end portion of the tubing attachment component. The external force required to rotate the frame may be predetermined or adjusted based on the friction provided by the locking protrusions. For example, the external force required may be extremely low so that the system can self-adjust to a neutral position to relieve tubing twist. The locking protrusions 425 allow the capture component and tubing attachment component to self-adjust and be fixed at a desired relative position, for example, a neutral position without tubing twist.

The tubing attachment component 44 has a conical body 444 with one or more radially outwardly extending barb 442 such as a hose barb, a flange 448 such as an annular flange, a plug or male fitting (male luer fitting) 446, and a central bore 441 formed through the tubing attachment component from the proximal end to the distal end. In one embodiment, a circumferential groove 447 is formed on the external surface of the tubing attachment component between the plug or male fitting 446 and the flange 448. The flange may be an annular flange.

The capture component 42 and the tubing attachment component 44 may be manufactured by injection molding and can be press-fitted together to create a tubing attachment system 40. In an assembled state, the capture component 42 is freely rotatable in the circumferential groove 447 provided on the tubing attachment component 44. Locking protrusions 425 are provided so that the assembly cannot be disassembled once fitted. The larger aspiration tube 24 slides into the barb 442 such that it is very difficult to remove the aspiration tube 24 once fitted. The freely rotating tubing attachment alleviates tubing twist. The electrical cable 26 has a small outer diameter, is located off-center from the axis of rotation, and is made with materials that provide enhanced flexibility. Socket or female fitting (female luer fitting) 122 on the handpiece forms an irrigation port for receiving the plug or male fitting (male luer fitting) 446.

FIGS. 8-11 show a capture component 542 of an embodiment of the present invention in more detail. The capture component 542 has a plurality of locking protrusions (or locking teeth or fingers) 525 disposed on the frame 521 extending inwardly, and two arms 527 curved towards each other for holding another tube, wire or other accessory. The locking protrusions 525 may be extending from an internal frame surface 524 of the frame 521, for example, extending from an internal frame surface 524 opposing the front surface 529 of the capture component 542, or extending radially inwardly from an internal frame surface 524 opposing the external frame surface 526 of the frame 521. Each locking protrusion has side walls 528 and a contact surface 522 facing a frame opening 523. The contact surface 522 of the plurality of locking protrusions 525 collectively provide adequate friction for holding or griping a tube or tubing attachment component received in the frame opening 523. The amount of torque needed to rotate the capture component 542 about a tubing attachment component may be established or changed by employing different numbers, geometries and/or materials of the locking protrusions, or by varying the curvatures or sizes of the contact surfaces of the locking protrusions. The frame has at least one locking protrusion, for example, 3-10 locking protrusions or preferably 4-8 locking protrusions. The locking protrusions may be integrally molded, fixedly connected or removeably attached to internal surface of the frame.

Figure 12A:
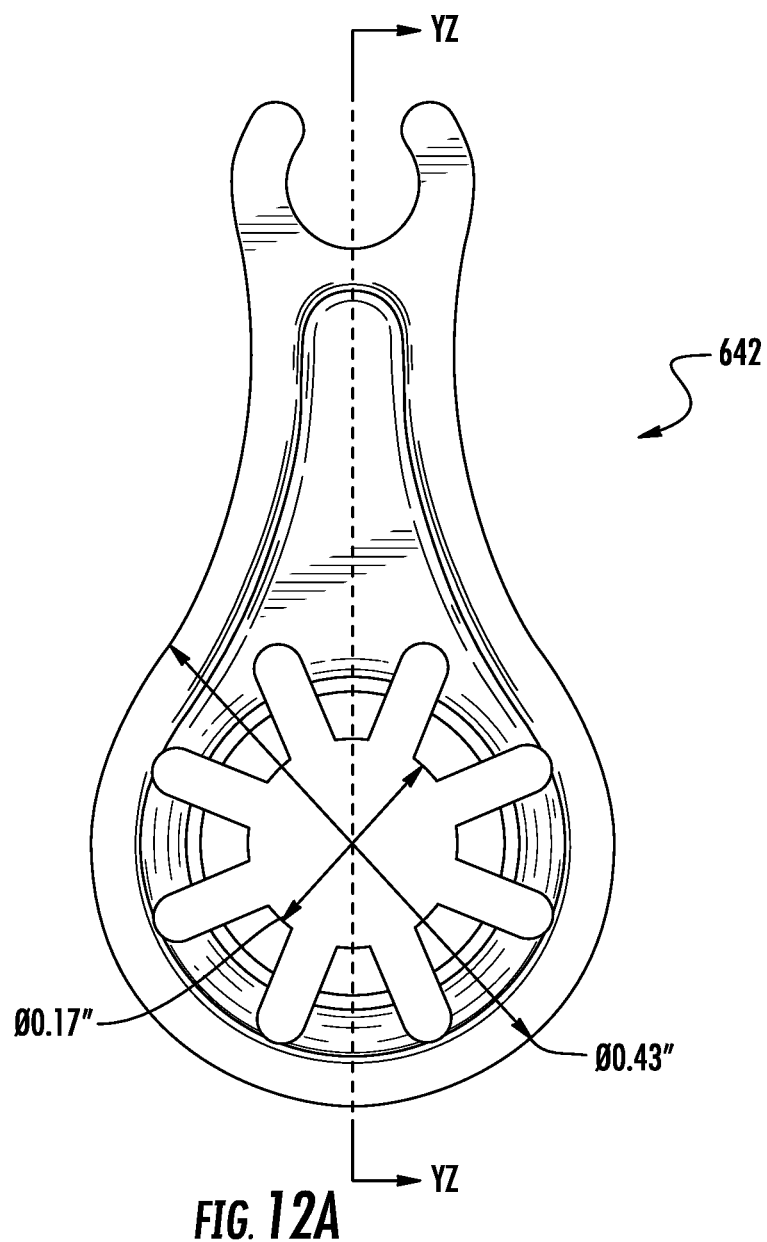
FIG. 12A is a rear view of another embodiment of a capture component of an embodiment of the present invention with dimensions shown in inches.
Figure 12B:
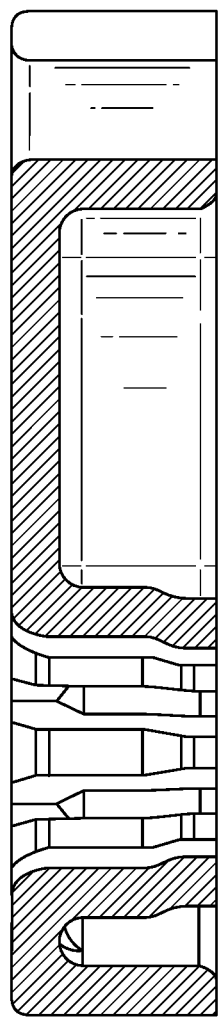
FIG. 12B is a cross-sectional view taken along line YZ-YZ of FIG. 12A.

FIG. 12 shows another embodiment of a capture component of the present invention. This capture component 642 embodiment has 8 locking protrusions, whereas the embodiment shown in previous drawings has 6 locking protrusions.

Although the frame of the capture component is shown to have a generally circular internal circumference and a generally circular external circumference, it is understood that the capture component in its entirety or the frame may have different configurations and shapes on its external surface and/or its internal surface, so long as the internal locking protrusions are arranged in a way that functions as a swivel joint in accordance with an embodiment of the present invention. Likewise, the locking protrusions may have different configurations, heights, widths or shapes so long as they jointly provide adequate friction to allow the swivel joint to rotate when an external force is applied and to frictionally lock the tubing attachment component in a desired position in the absence of such external force.

Figure 13:
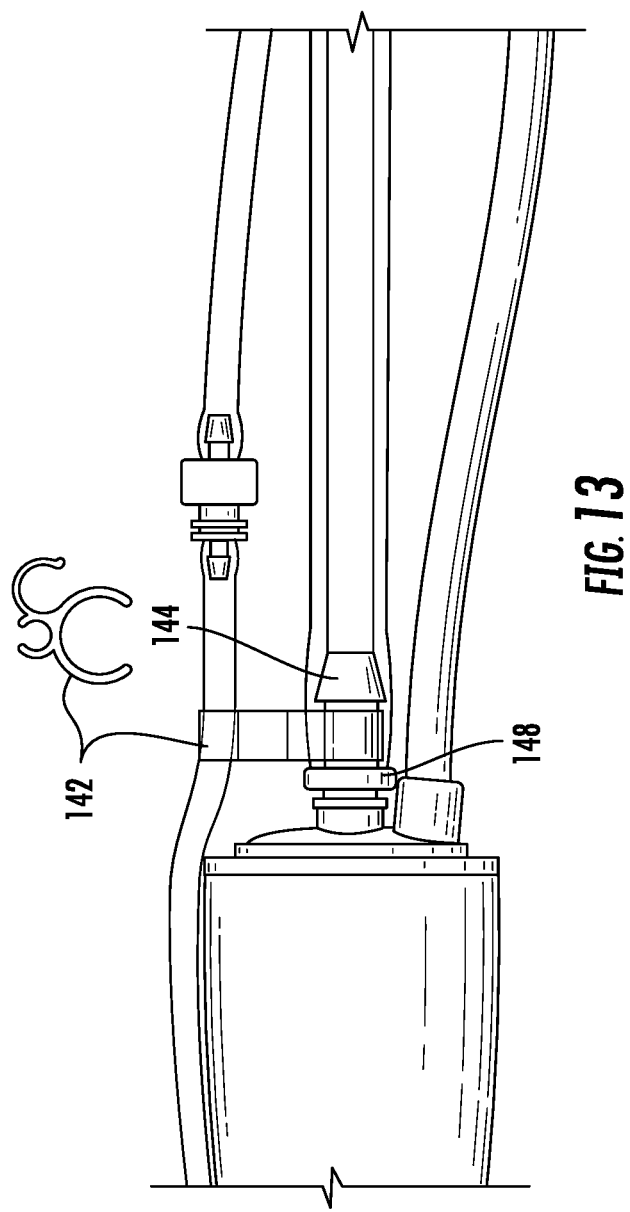
FIG. 13 illustrates an alternative embodiment of a tubing attachment system of an embodiment of the present invention in an assembled and connected state and additionally includes a detailed view of the capture component.

FIGS. 13-18 illustrate additional variations of the capture component and/or the tubing attachment component in their general configurations without showing the locking protrusions of the capture component. FIG. 13 shows embodiments of a capture component 142 and a tubing attachment component 144. The molded tubing clip or capture component 142 is assembled to or about an aspiration tube 24 to bundle the aspiration tube and irrigation tube, power cord and CEM along the length of the tubing set. The tubing attachment component 144 has a flange 148 positioned distally to the capture component 142 in an assembled state.

Figure 14:
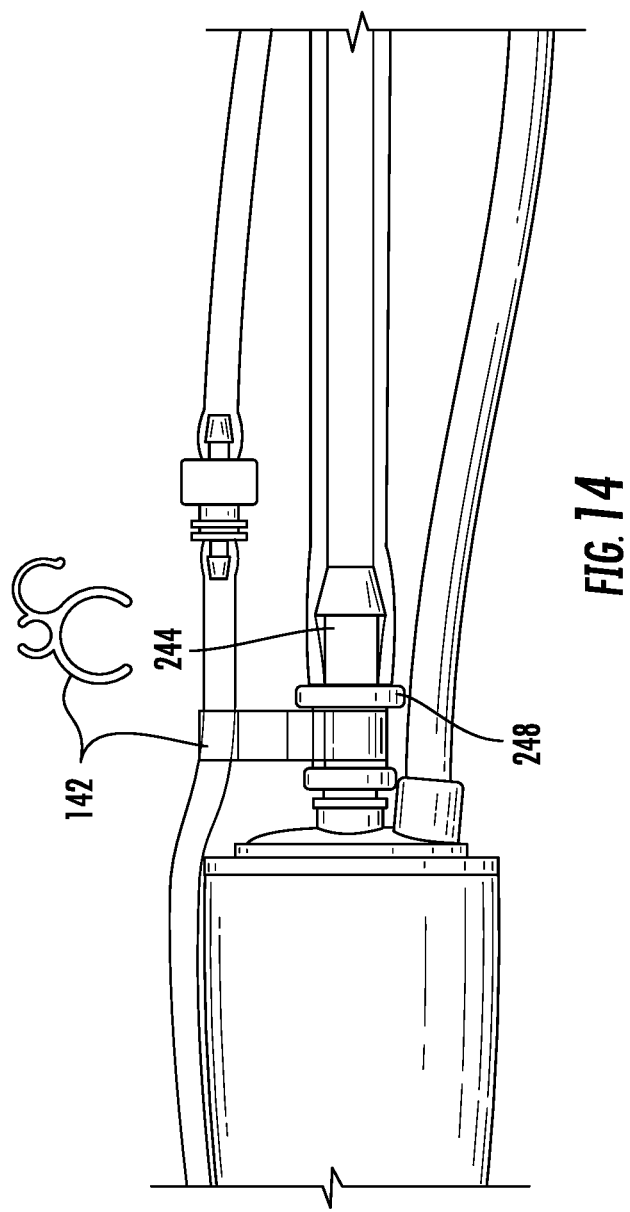
FIG. 14 illustrates another alternative embodiment of a tubing attachment system of an embodiment of the present invention in an assembled and connected state and additionally includes a detailed view of the capture component.

FIG. 14 shows another alternative embodiment of a tubing attachment component 244. It has a flange 248 positioned proximally to the capture component 142 in an assembled state.

Figure 15:
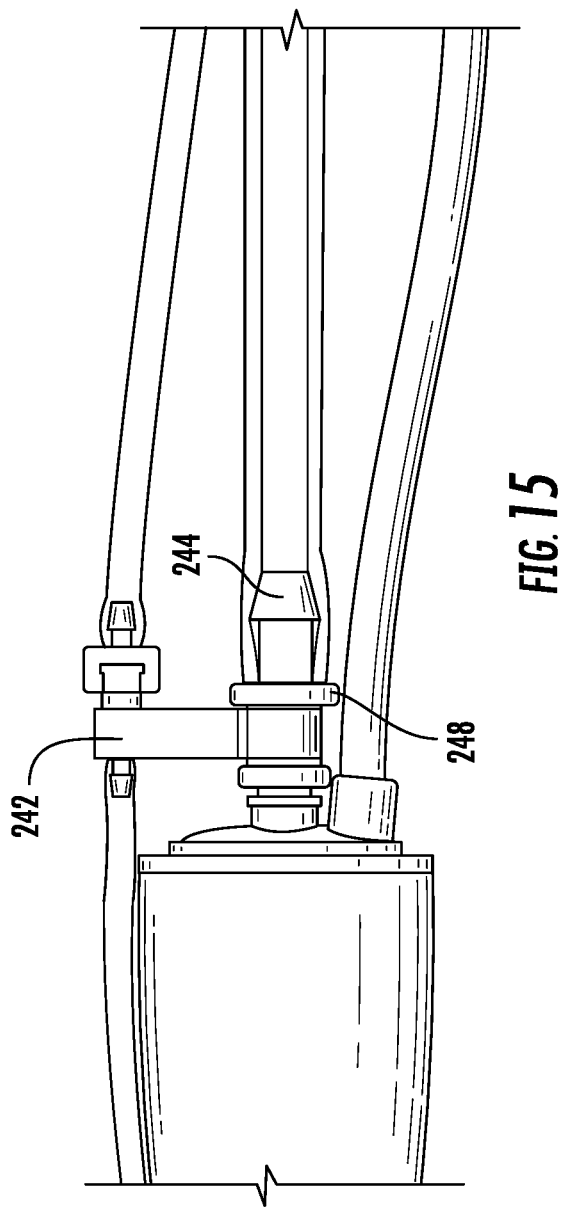
FIG. 15 illustrates a further alternative embodiment of a tubing attachment system of an embodiment of the present invention in an assembled and connected state.

FIG. 15 shows another embodiment of a capture device 242. The capture component is assembled to the end of the flue tube, clips on to the aspiration tube luer fitting or tubing attachment component 244. The flue would have a shorter length of flue tube and a custom connector for connection with the irrigation tube.

The swivel joint formed by the tubing attachment component and the capture component allows the tube to rotate circumferentially with respect to the handpiece without axial displacement of the tube. Although exemplary embodiments are described herein, it is contemplated that swivel joints with other configurations or mechanisms, including but not limited to commercially available swivel joints, may be used without departing from the spirit of the present invention.

FIG. 16 shows a female luer lock flue tube fitting 345 assembled to an end of the flue tube. It may be stretched slightly and clips onto the rear nut 343. An annular groove 347 is machined into the rear nut and provides a channel to accept the flue tube fitting. The flue has a shorter length of flue tubing than the flue tubing as shown in FIG. 15.

FIG. 17 shows that a ring 535 with a clip is trapped by a rear cap 547 and can rotate to accept a flue tube in any position. The durable molded rear cap is snapped on to the rear nut semi-permanently to protect the potting from staining.

FIG. 18 shows a disposable molded rear cap 647, with a dog house cut out for power cord. It is snapped on to rear nut to protect the potting from staining. The rear cap 647 may be assembled to the aspiration tube, but still allows the tubing attachment component to be rotated to alleviate torque. A C-clip 637 with a clip for flue tube is snapped onto a groove in the disposable rear cap.

Figure 19A:
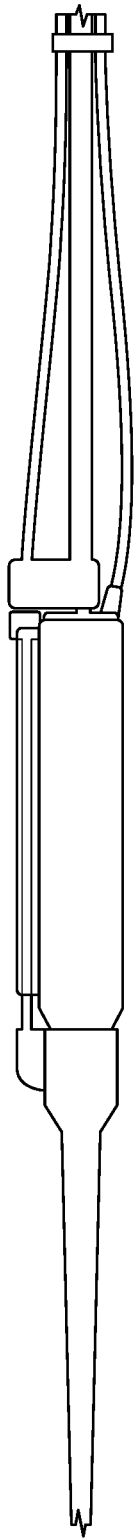
FIG. 19A illustrates a prior art tubing connection architecture.
Figure 19B:
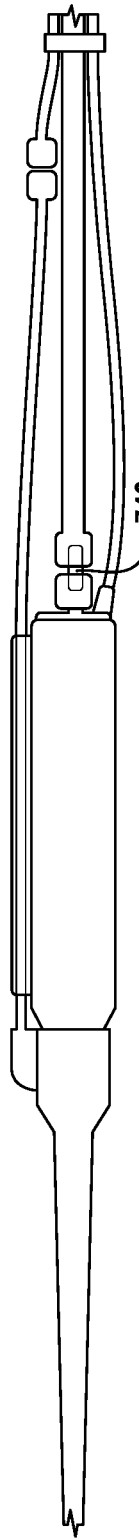
FIGS. 19B and 19C illustrate various embodiments of tubing connection architectures.
Figure 19C:
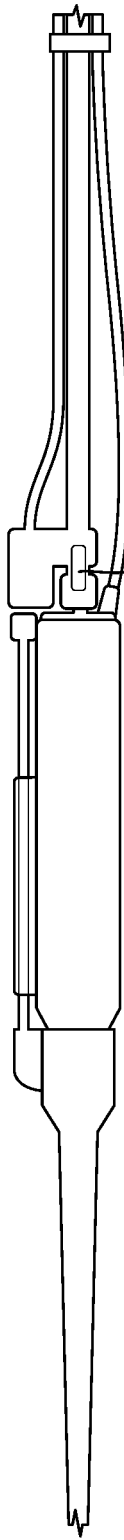

FIGS. 19A-C illustrate various embodiments of tubing connection architectures. The tubing connection in FIG. 19A shows a prior art tubing connection architecture that does not have any swivel according to an embodiment of the present invention. FIG. 19B illustrates that the swivel joint of an embodiment of the present invention is present in the suction line only. FIG. 19C illustrates that the swivel joint applies to both the suction and irrigation tubing connections. The swivel joint of an embodiment of the present invention may be present in the suction/aspiration tubing connection and/or the flue tubing and irrigation tubing connection. The swivel joint may also be present on the power cable connection.

Figure 20A:
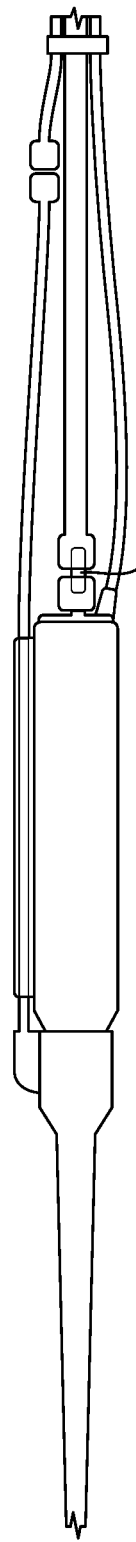
Figure 20B:
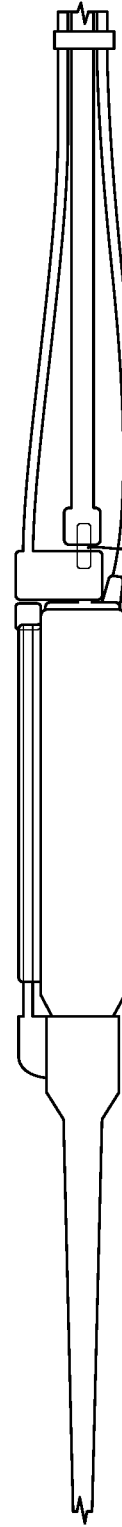

As shown in FIGS. 20A-E, the flue, flue tube, and irrigation tube may be connected in various configurations. For example, the flue tube may connect to the irrigation tube at a point proximal to the handpiece, near to the rear cap of the handpiece, or near the flue, or at a suction connector or a stationary portion of a tubing connector. Alternatively, the irrigation tube may connect directly to the flue, without the need for a flue tube. The flue tube may be captured in a slot that runs along the entire length of the handpiece or along a portion of the length of the handpiece. Each of the various embodiments include a swivel joint 740. FIG. 20A shows that the flue tube connects to the irrigation tube down-stream and captured in a slot along the length of the handpiece. FIG. 20B shows that the flue tube connects to the irrigation tube at a stationary portion of the tubing connector. FIG. 20C shows that the flue tube connects to the irrigation tube at a suction connector (service loop). FIG. 20D shows that the flue tube connects to the irrigation tube a suction connector in a different way (exposed flue tube). FIG. 20E shows that the irrigation tube connects to the flue.

Suitable materials for making the tubing attachment component and capture component including locking protrusions, include, but are not limited to, natural or synthetic materials, for example, metal, polymeric or thermoplastic materials. Examples include silicone, nylon, polypropylene, polycarbonate, polytetrafluoroethylene (PTFE), polyetheretherketone (PEEK), polyetherimide (PEI) resins, polyphenylsulfone (PPSU), or polysulfone, or other materials known to those skilled in art, or combinations of the above. The capture component can be made by injection molding or other conventional manufacturing methods. The components and portions thereof may be made of different materials. It may be preferred to use durable materials that can survive steam sterilizations or other sterilization processes. The components may be made of low cost materials for use as disposable components.

The materials of the tubing and locking protrusions and their finishes are chosen such that the friction between the surfaces is minimal and the tubing can freely rotate on the hose barb even under the vacuum of aspiration. Additional materials and structures of tubing may be developed or selected to reduce twisting. It is also possible to provide dynamic relief of twisting using biomimetic tubing design and/or nano-structured surface finish to reduce friction.

The tubing attachment system or assembly of an embodiment of the present invention has many advantages. With respect to ergonomics, the tubing attachment provides neutralization and adjustment of force due to twist of tubing which was identified as a major factor in surgeon fatigue involving muscles of the thumb, other fingers and wrist. In addition, connectors may be made of plastic which is light weight compared to metal luer fittings used in prior art and the coefficient of friction between the tubing silicone and connector polymer can be tuned by molding surface finish to create low torsional resistance to dynamic adjustment. Furthermore, irrigation and aspiration connectors can be gathered together for ease of tubing management while their rotational orientation can be independently adjusted for comfort. With respect to electrical safety for electrosurgical or combination electrosurgical and ultrasonic handpieces, the connectors may be made of non-conducting plastic which results in simpler design for electrosurgical devices with high voltage that can be induced or conduced in metal parts. With respect to manufacturing cost, connectors can be molded at high volume at minimal cost such that they can be disposable.

The tubing attachment system and swivel joint described above could be useful for ultrasonic surgical apparatus, electrosurgical apparatus, rotational drill type instruments, or other instruments, whether powered or not, that have tubing such as irrigation tubing or aspirating tubing, wiring or cables.

Figure 21A:
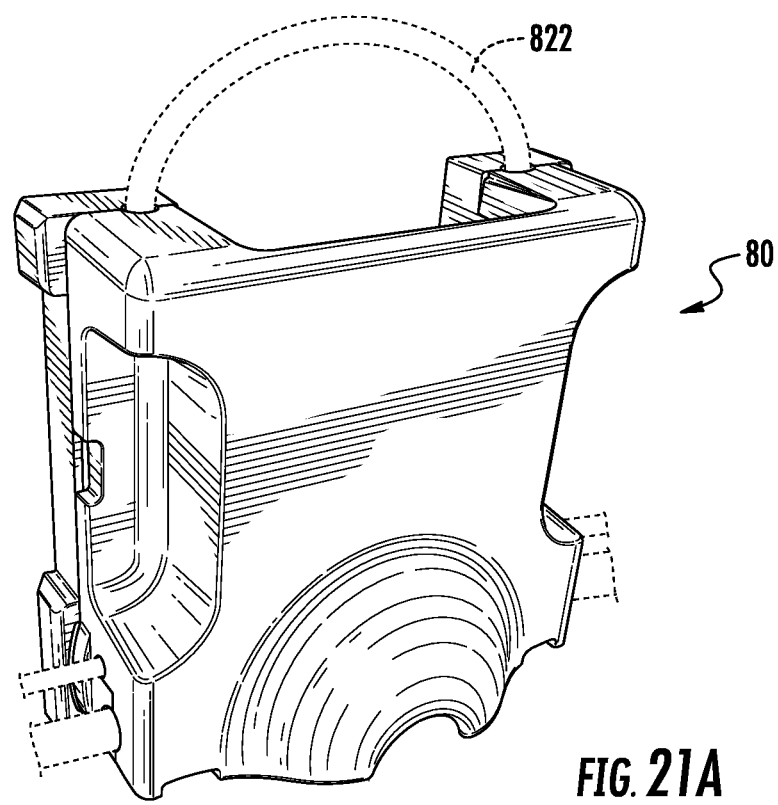
FIG. 21A is a perspective view of a tubing cartridge in accordance with an embodiment of the present invention.
Figure 21B:
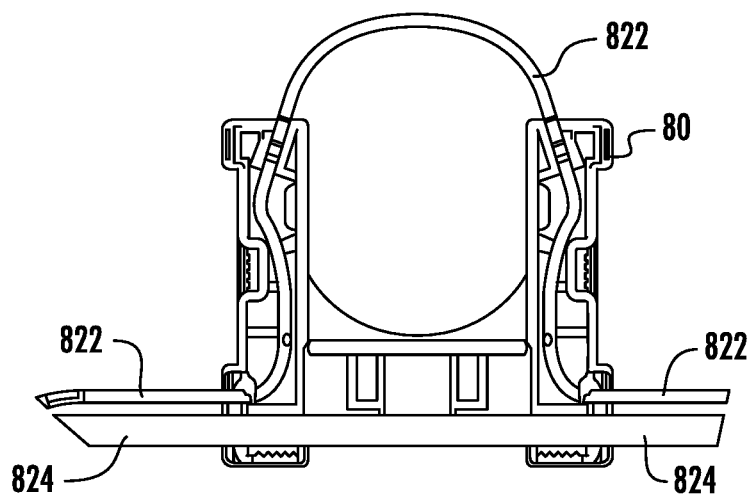
FIG. 21B is an assembly showing the path of the irrigation and aspiration tubing within the cartridge.
Figure 21C:
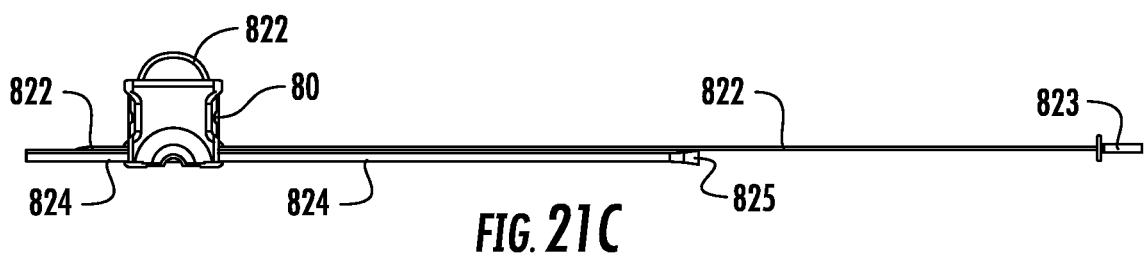
FIG. 21C is an assembly drawing showing aspiration and IV connectors on the right.

In addition to the tubing attachment to the handpiece, another tubing attachment issue in medical apparatus is also addressed. As described above, tubing sets for ultrasonic aspirators consist of at least two lumens. One lumen has a smaller diameter intended to supply irrigation to the sterile field through the handpiece. The other lumen has a larger diameter and is intended to provide a path for aspiration from the sterile field to a collection canister near the console. Tubing in the commercial ultrasonic aspirators on the market is seen as difficult to handle and assemble to the console due to the fact that the user has to know how to align it in the pump and pinch valve at the console and the need to have a secondary tubing assembly to connect to an IV bag. To address this issue, an embodiment of the present invention provides a tubing cartridge 80 as shown in FIG. 21A that allows alignment of both sets of tubing, i.e., the irrigation tubing 822 and aspiration tubing 824, in one motion on the console and has an integral IV bag spike or IV connector 823 so a secondary tubing is not needed. FIG. 21B shows an assembly with the path of the irrigation and aspiration tubing within the cartridge 80. FIG. 21C shows an aspiration canister connector 825 and an IV connector 823 on the right.

Figure 22A:
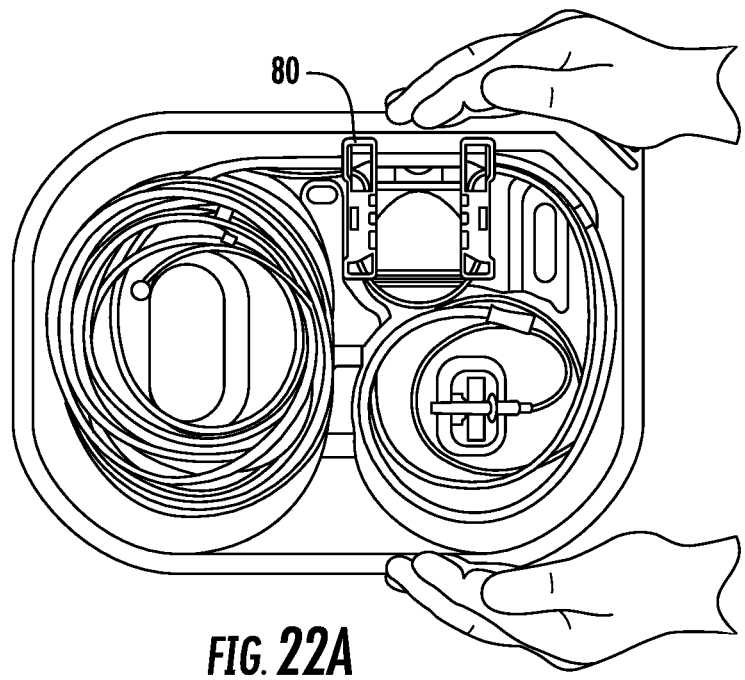
FIGS. 22A, 22B, 22C, 22D, 22E, and 22F show a step-by-step process of connecting a cartridge and tubing set of an embodiment of the present invention to a handpiece.
Figure 22B:
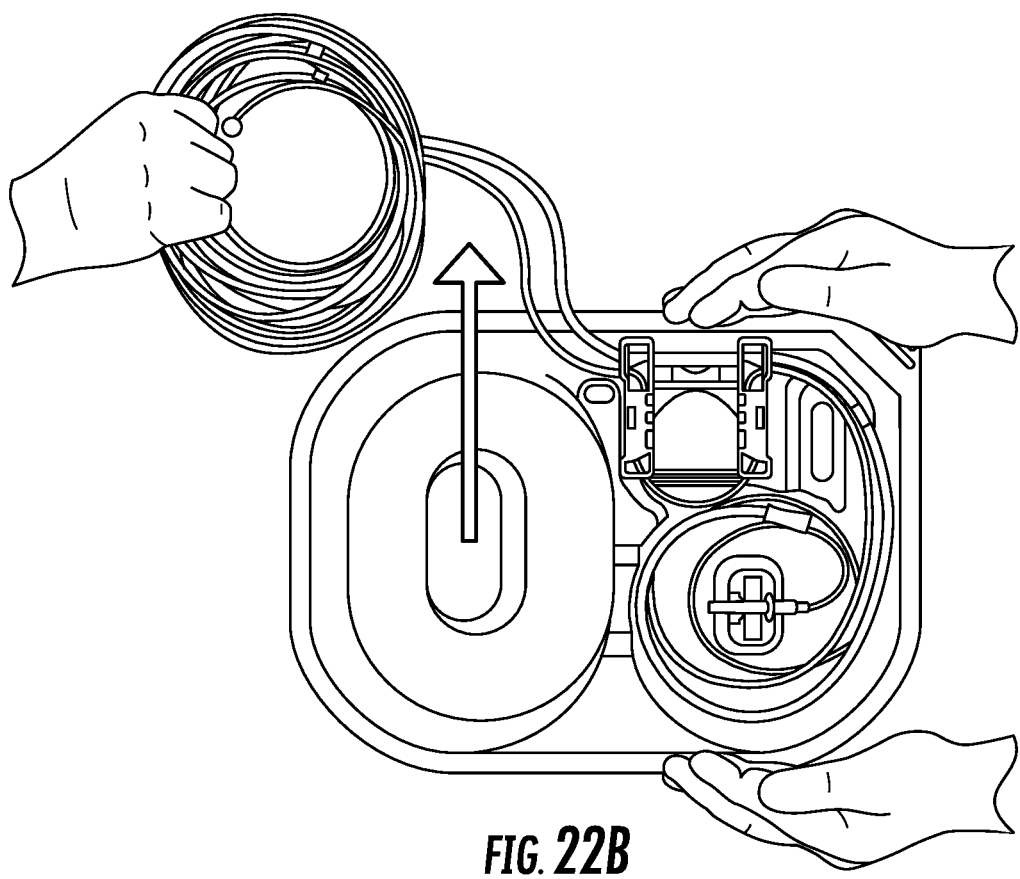
Figure 22C:
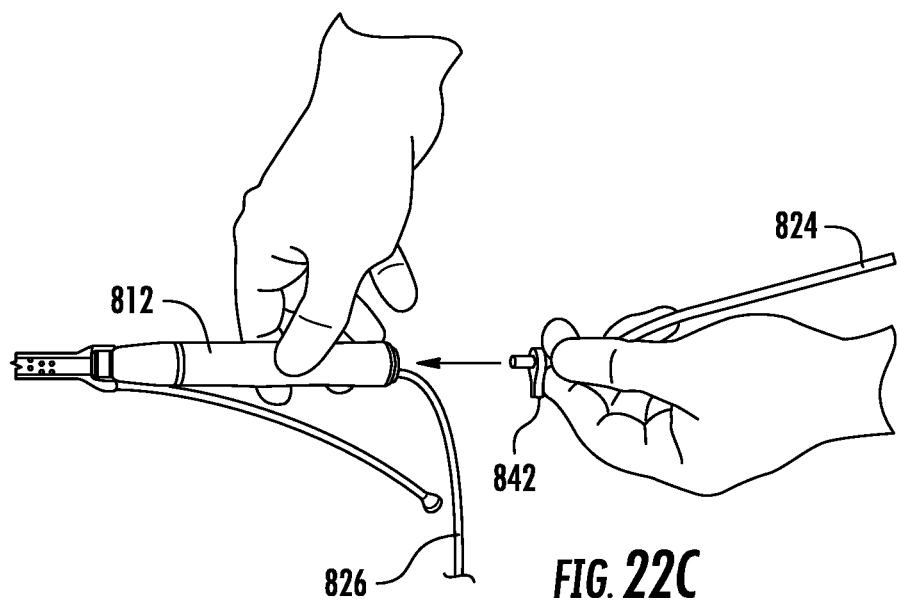
Figure 22D:
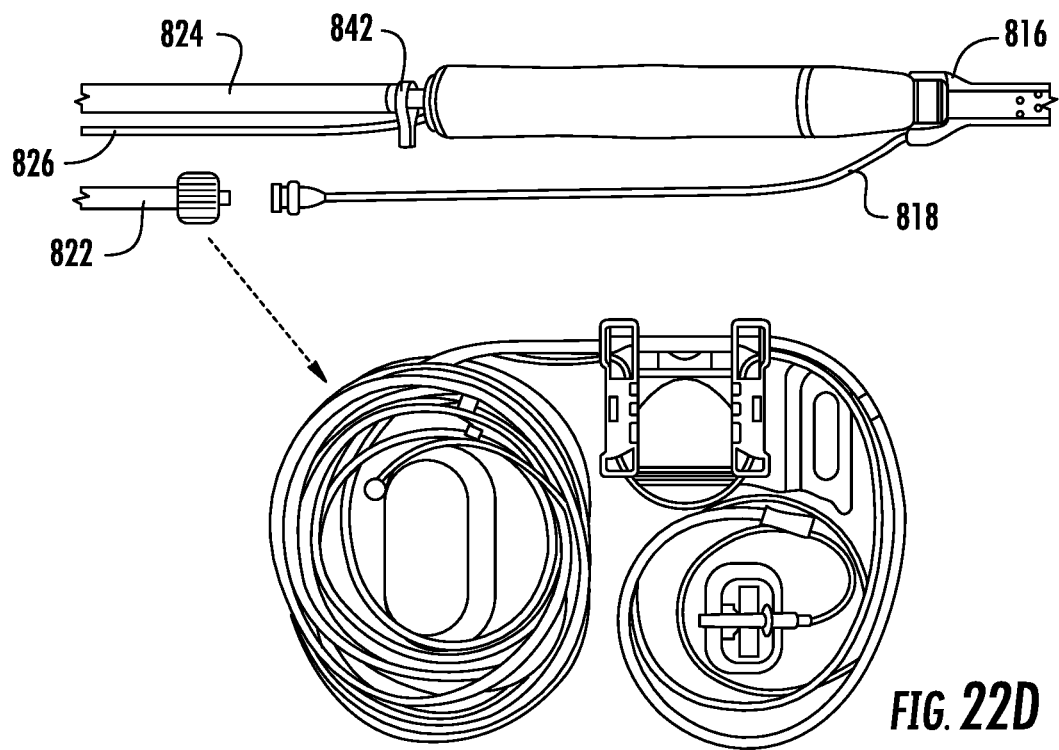
Figure 22E:
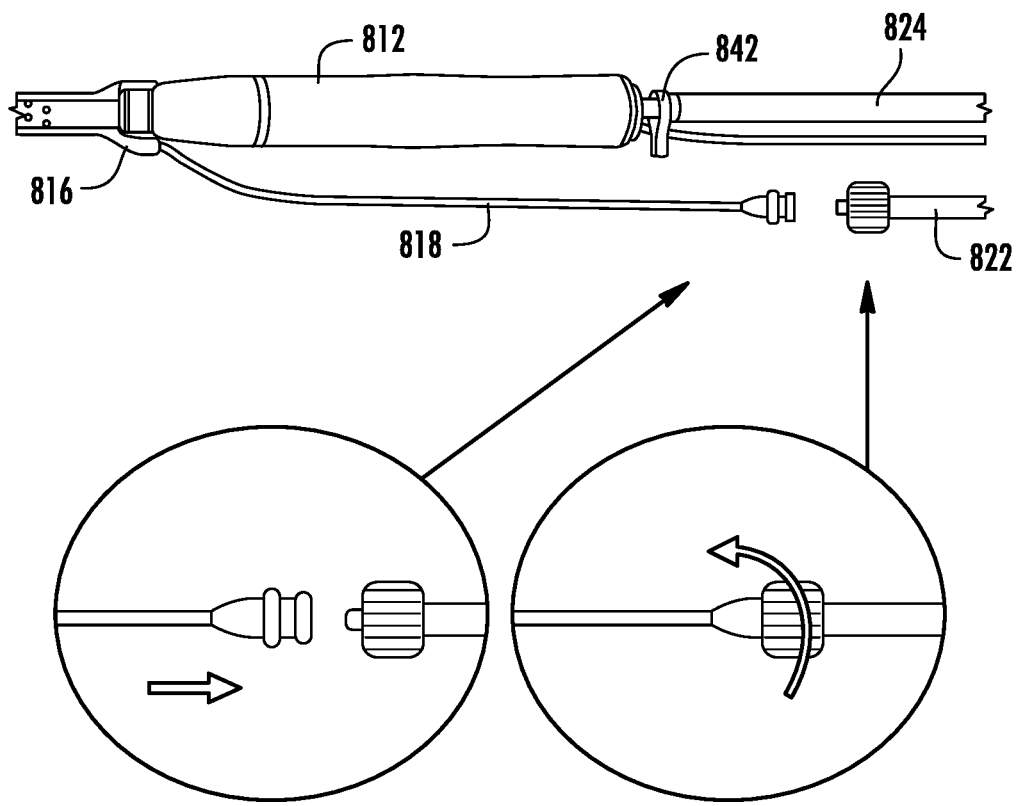
Figure 22F:
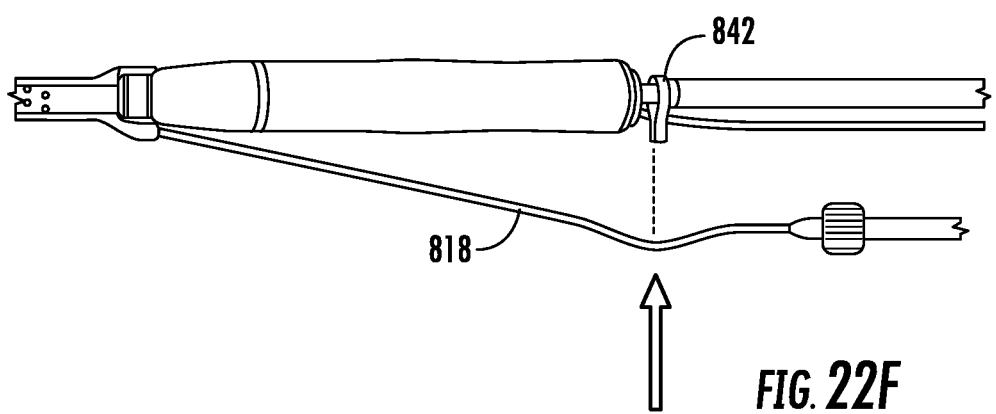

In terms of use, a sterile user would assemble the tubing set to the handpiece in the sterile field. FIG. 22A shows a cartridge and tubing set. As shown in FIG. 22B, to assemble the tubing set to the handpiece 812, the user should first pick up the larger loop of the irrigation and aspiration tubing set to be brought into the sterile field and assembled to the handpiece 812. The handpiece 812 has an electrical cable 826. Place the cartridge and smaller loop of the irrigation and aspiration tubing set aside until it is time to connect it to the console. As shown in FIG. 22C, attach the aspiration tubing 824 to the aspiration port at the base of the handpiece. As shown in FIGS. 22D and 22E, attach the irrigation tubing 822 to the luer lock fitting on the handpiece flue tubing 818 of the flue 816. As shown in FIG. 22F, push the irrigation tubing and flue tubing 818 into the capture component or tubing clip 842 at the base of the handpiece. The tubing clip allows for adjustment of location of the flue/irrigation tubing based on the desires of the surgeon.

Figure 23A:
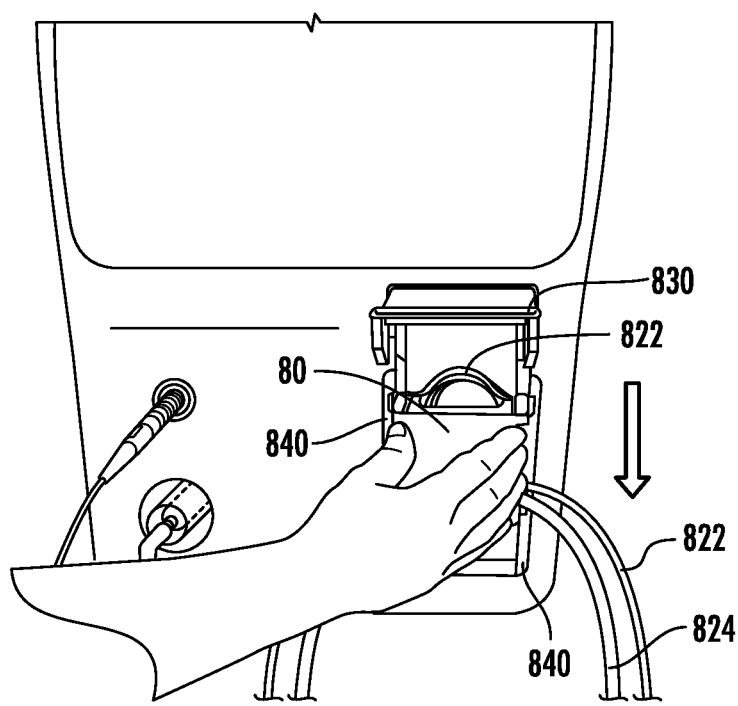
FIGS. 23A, 23B, 23C, and 23D show a step-by-step process of connecting a cartridge and tubing set of an embodiment of the present invention to a console of an ultrasonic aspirator.
Figure 23B:
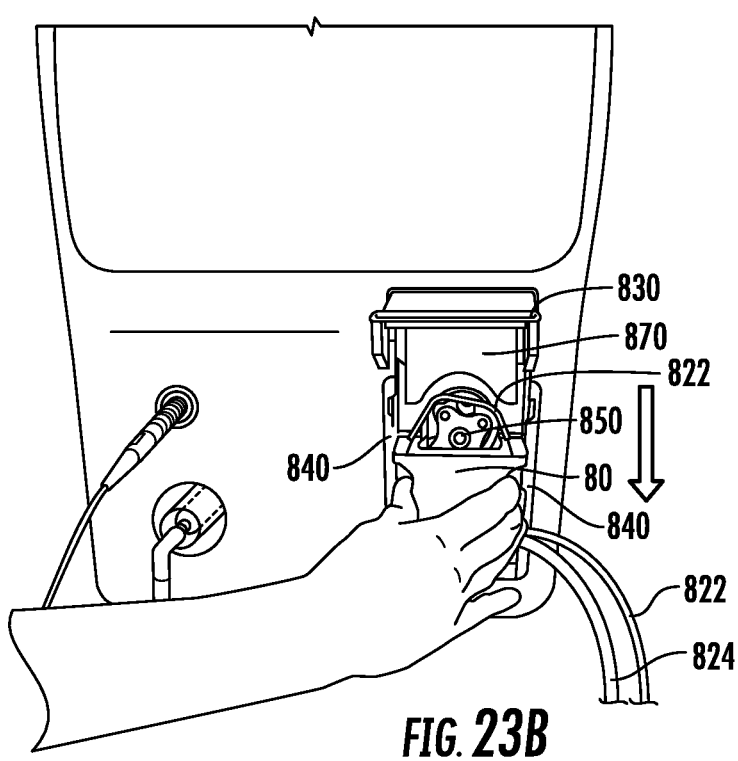
Figure 23C:
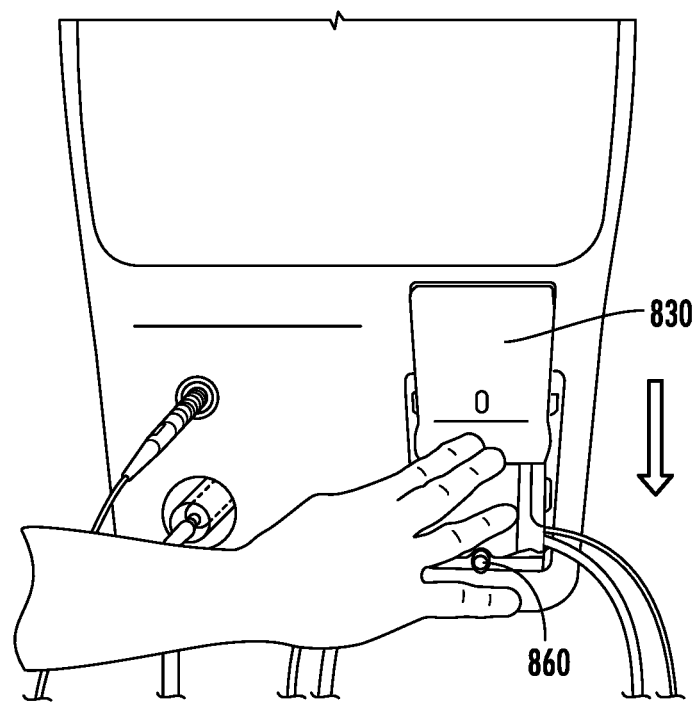
Figure 23D:
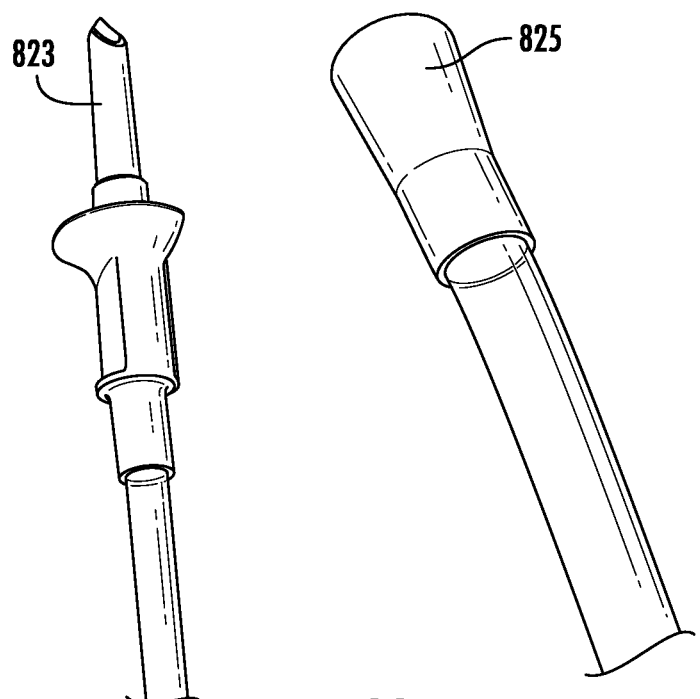

The remainder of the assembly would then be passed to non-sterile personnel for connection to the console, as shown in FIGS. 23A-23D. In the non-sterile area, a user opens the irrigation door 830 and align the cartridge 80 with runners 840, as shown in FIG. 23A. The user will then push the cartridge 80 down to align with the peristaltic wheel 850 and pinch valve 860 in one motion. This will also impart the appropriate amount of "stretch" on the irrigation tubing 822 to assure proper function during use, as shown in FIG. 23B. The door 830 is then closed which secures the cartridge 80 and allows the backing wall 870 to compress the tubing for proper function, as shown in FIG. 23C. Final steps are to connect the IV connector 823 and the aspiration canister connector 825 shown in FIG. 23D to an IV bag and an aspiration canister, respectively. The tubing cartridge allows the user to quickly connect the tubing set to the console.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention may be embodied in other forms without departure from the scope and essential characteristics thereof. The embodiments described therefore are to be considered in all respects as illustrative and not restrictive. Although the present invention has been described in terms of certain preferred embodiments, other embodiments that are apparent to those of ordinary skill in the art are also within the scope of the invention.

The invention claimed is:

1. A tubing attachment system comprising:
 a tubing clip having a frame having an internal frame surface, an external frame surface, and a frame opening defining a longitudinal axis, the frame including at least one locking protrusion extending inward from the internal frame surface, and wherein the at least one locking protrusion defines the frame opening, and wherein the tubing clip includes one or more tube retaining arms extending outwardly from the frame;
 a tubing attachment component having a proximal end, a distal end, and an external surface, the tubing attachment component comprising a proximal end portion configured to attach to the tube, a distal end portion configured to attach to the handpiece, a throughbore extending from the distal end to the proximal end, and a circumferential groove on the external surface between the proximal end portion and the distal end portion;
 wherein the frame and the at least one locking protrusion are configured to fit in the circumferential groove and be rotatable in the circumferential groove about the tubing attachment component when an external force is applied and to frictionally lock the tubing attachment component in a desired rotational position in the absence of such external force;
 wherein the proximal end portion includes a conical body transitioning into a radially outwardly extending barb for securing the tube, and the distal end portion includes a fitting for engaging a corresponding fitting on the handpiece; and
 wherein the tubing attachment component further comprises a flange between the conical body and the fitting, and the flange forms a rail of the circumferential groove.

2. The tubing attachment system of claim 1, wherein the tubing clip includes one or more channels defined by the one or more tube retaining arms.

3. The tubing attachment system of claim 1, wherein the at least one protrusion includes a contact surface facing inwardly that extends from a proximal end to a distal free end of the at least one locking protrusion.

4. The tubing attachment system of claim 2, wherein the one or more channels and the frame opening are parallel to each other.

5. The tubing attachment system of claim 1, wherein the tubing clip includes a plurality of the at least one locking protrusion spaced circumferentially about the frame opening.

6. The tubing attachment system of claim 1, in combination with an ultrasonic surgical apparatus having a handpiece and a tube connected to the proximal end portion of the tubing attachment component.

7. A tubing attachment system comprising:
 a tubing clip having a frame having an internal frame surface, an external frame surface, and a frame opening defining a longitudinal axis, the frame including at least one locking protrusion extending inward from the internal frame surface, and wherein the at least one locking protrusion defines the frame opening, and wherein the tubing clip includes one or more tube retaining arms extending outwardly from the frame;
 wherein the at least one locking protrusion includes a first contact surface facing inwardly that extends from a proximal end to a distal free end of the at least one locking protrusion; and
 wherein the at least one locking protrusion includes a second contact surface at the distal free end facing axially away from the frame in a direction along the longitudinal axis.

8. The tubing attachment system of claim 7, wherein the tubing clip has a plurality of the at least one locking protrusion disposed on the internal frame surface of the frame.

9. The tubing attachment system of claim 7, wherein the one or more tube retaining arms form a channel configured to hold another tube.

10. The tubing attachment system of claim 7, further comprising a tubing attachment component having a proximal end, a distal end, and an external surface, the tubing attachment component comprising a proximal end portion configured to attach to the tube, a distal end portion configured to attach to the handpiece, a throughbore extending from the distal end to the proximal end, and a circumferential groove on the external surface between the proximal end portion and the distal end portion;
   wherein the frame and the at least one locking protrusion are configured to fit in the circumferential groove and be rotatable in the circumferential groove about the tubing attachment component when an external force is applied and to frictionally lock the tubing attachment component in a desired rotational position in the absence of such external force;
   wherein the proximal end portion includes a conical body transitioning into a radially outwardly extending barb for securing the tube, and the distal end portion includes a fitting for engaging a corresponding fitting on the handpiece; and
   wherein the tubing attachment component further comprises a flange between the conical body and the fitting, and the flange forms a rail of the circumferential groove.

11. The tubing attachment system of claim 7, in combination with a medical apparatus, wherein the medical apparatus is an ultrasonic surgical apparatus.

12. A medical apparatus comprising:
   a handpiece and a tube, wherein the tube is connected to the handpiece through a swivel joint which allows the tube to rotate circumferentially with respect to the handpiece without axial displacement of the tube; and
   wherein the swivel joint further comprises:
   a tubing attachment component having a longitudinal throughbore and a circumferential groove on an external frame surface, wherein a bottom wall of the circumferential groove increases in depth towards the longitudinal throughbore; and
   a tubing clip having a frame with a frame opening defining a longitudinal axis and at least one locking protrusion having a first contact surface facing inwardly and narrowing the frame opening along the longitudinal axis, wherein the first contact surface of the at least one locking protrusion extends from a proximal end to a distal free end of the at least one locking protrusion, wherein the first contact surface of the at least one locking protrusion contours to and frictionally engages the bottom wall of the circumferential groove of the tubing attachment component, and wherein the at least one locking protrusion includes a second contact surface at the distal free end facing axially away from the frame in a direction along the longitudinal axis;
   wherein the frame can be snapped into the circumferential groove of the tubing attachment component and rotate about the tubing attachment component; and
   wherein the at least one locking protrusion allows the tubing clip and tubing attachment component to be fixed at a desired relative position.

13. The medical apparatus of claim 12, wherein the tubing clip includes a plurality of the at least one locking protrusion extending radially inward from an internal frame surface of the frame.

14. The medical apparatus of claim 12, wherein the tubing attachment component further comprises a flange extending from the external frame surface of the tubing attachment component and defining a longitudinal extent of the circumferential groove.

15. The medical apparatus of claim 12, wherein the tubing clip further comprises one or more arms extending outwardly from an external frame surface forming one or more channels for holding another tube.

16. The medical apparatus of claim 12, which is an ultrasonic surgical apparatus and wherein the tube is an irrigation tube or an aspiration tube.

* * * * *